US010271791B2

(12) United States Patent
Donnelly et al.

(10) Patent No.: US 10,271,791 B2
(45) Date of Patent: *Apr. 30, 2019

(54) WEARABLE MEDICAL MONITORING DEVICE

(71) Applicant: ZOLL MEDICAL CORPORATION, Chelmsford, MA (US)

(72) Inventors: Edward J. Donnelly, Allison Park, PA (US); Thomas E. Kaib, Irwin, PA (US); Marshal W. Linder, New Kensington, PA (US); Steven J. Szymkiewicz, Bethel Park, PA (US); Jason T. Whiting, Gibsonia, PA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,739

(22) Filed: Jul. 14, 2017

(65) Prior Publication Data
US 2018/0014779 A1    Jan. 18, 2018

Related U.S. Application Data

(63) Continuation of application No. 15/010,778, filed on Jan. 29, 2016, now Pat. No. 9,737,262, which is a
(Continued)

(51) Int. Cl.
*A61B 5/00* (2006.01)
*A61B 5/0205* (2006.01)
(Continued)

(52) U.S. Cl.
CPC ........ *A61B 5/6804* (2013.01); *A61B 5/02055* (2013.01); *A61B 5/11* (2013.01);
(Continued)

(58) Field of Classification Search
CPC ...... A61B 2560/045; A61B 2562/0219; A61B 5/02055; A61B 5/021; A61B 5/02438;
(Continued)

(56) References Cited

U.S. PATENT DOCUMENTS

| 4,094,310 A | 6/1978 | McEachern et al. |
| 4,432,368 A | 2/1984 | Russek |

(Continued)

FOREIGN PATENT DOCUMENTS

| CN | 101031334 A | 9/2007 |
| CN | 101848677 A | 9/2010 |

(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.
(Continued)

*Primary Examiner* — George Manuel
(74) *Attorney, Agent, or Firm* — ZOLL Medical Corporation

(57) ABSTRACT

A wearable monitoring device includes a plurality of cardiac sensing electrodes, a monitor, at least one motion sensor, and a controller. The plurality of cardiac sensing electrodes are positioned outside a body of a subject and to detect cardiac information of the subject. The monitor administers a predetermined test to the subject, and has a user interface configured to receive quality of life information from the subject. The at least one motion sensor is positioned outside the body of the subject and to detect subject motion during the predetermined test. The controller is communicatively coupled to the plurality of cardiac sensing electrodes, the monitor, and the at least one motion sensor, and receives and
(Continued)

stores the detected cardiac information, the quality of life information, and the detected subject motion.

36 Claims, 7 Drawing Sheets

Related U.S. Application Data continuation of application No. 14/175,433, filed on Feb. 7, 2014, now Pat. No. 9,283,399, which is a continuation of application No. 13/416,734, filed on Mar. 9, 2012, now Pat. No. 8,649,861, which is a continuation of application No. 12/833,173, filed on Jul. 9, 2010, now Pat. No. 8,140,154, which is a continuation-in-part of application No. 12/002,469, filed on Dec. 17, 2007, now Pat. No. 7,974,689.

(60) Provisional application No. 60/934,404, filed on Jun. 13, 2007.

(51) Int. Cl.
| | |
|---|---|
| *A61B 5/11* | (2006.01) |
| *A61N 1/04* | (2006.01) |
| *A61N 1/365* | (2006.01) |
| *A61N 1/372* | (2006.01) |
| *A61N 1/39* | (2006.01) |
| *G16H 40/63* | (2018.01) |
| *G16H 50/20* | (2018.01) |
| *A61B 5/021* | (2006.01) |
| *A61B 5/024* | (2006.01) |
| *A61B 5/0408* | (2006.01) |
| *A61B 5/08* | (2006.01) |
| *A61B 5/1455* | (2006.01) |

(52) U.S. Cl.
CPC ........... *A61B 5/1112* (2013.01); *A61B 5/1117* (2013.01); *A61B 5/4818* (2013.01); *A61B 5/6805* (2013.01); *A61N 1/0484* (2013.01); *A61N 1/36585* (2013.01); *A61N 1/37258* (2013.01); *A61N 1/39* (2013.01); *A61N 1/3987* (2013.01); *A61N 1/3993* (2013.01); *G16H 40/63* (2018.01); *G16H 50/20* (2018.01); *A61B 5/021* (2013.01); *A61B 5/02438* (2013.01); *A61B 5/04085* (2013.01); *A61B 5/0816* (2013.01); *A61B 5/1455* (2013.01); *A61B 5/721* (2013.01); *A61B 2560/045* (2013.01); *A61B 2562/0219* (2013.01); *A61N 1/36535* (2013.01); *A61N 1/36542* (2013.01); *A61N 1/37247* (2013.01)

(58) Field of Classification Search
CPC ..... A61B 5/04085; A61B 5/0816; A61B 5/11; A61B 5/1112; A61B 5/1117; A61B 5/1455; A61B 5/4818; A61B 5/6804; A61B 5/6805; A61B 5/721; A61N 1/0484; A61N 1/36535; A61N 1/36542; A61N 1/36585; A61N 1/37247; A61N 1/37258; A61N 1/39; A61N 1/3987; A61N 1/3993; G16H 40/63; G16H 50/20
See application file for complete search history.

(56) References Cited

U.S. PATENT DOCUMENTS

| | | | |
|---|---|---|---|
| 4,632,122 A | 12/1986 | Johansson et al. | |
| 4,698,848 A | 10/1987 | Buckley | |
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,176,380 A | 1/1993 | Evans et al. | |
| 5,330,505 A | 7/1994 | Cohen | |
| 5,348,008 A | 9/1994 | Bornn et al. | |
| 5,353,793 A | 10/1994 | Bornn | |
| 5,357,696 A | 10/1994 | Gray et al. | |
| 5,365,932 A | 11/1994 | Greenhut | |
| 5,472,453 A | 12/1995 | Alt | |
| 5,544,661 A * | 8/1996 | Davis ................... | A61B 5/0002 600/513 |
| 5,564,429 A | 10/1996 | Bornn et al. | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,065,154 A | 5/2000 | Hulings et al. | |
| 6,097,982 A | 8/2000 | Glegyak et al. | |
| 6,097,987 A | 8/2000 | Milani | |
| 6,148,233 A | 11/2000 | Owen et al. | |
| 6,169,387 B1 | 1/2001 | Kaib | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,406,426 B1 | 6/2002 | Reuss et al. | |
| 6,666,830 B1 | 12/2003 | Lehrman et al. | |
| 6,681,003 B2 | 1/2004 | Linder et al. | |
| 6,690,969 B2 | 2/2004 | Bystrom et al. | |
| 6,790,178 B1 | 9/2004 | Mault et al. | |
| 6,804,554 B2 | 10/2004 | Ujhelyi et al. | |
| 6,827,695 B2 | 12/2004 | Palazzolo et al. | |
| 6,865,413 B2 | 3/2005 | Halperin et al. | |
| 6,908,437 B2 | 6/2005 | Bardy | |
| 6,944,498 B2 | 9/2005 | Owen et al. | |
| 6,990,373 B2 | 1/2006 | Jayne et al. | |
| 7,074,199 B2 | 7/2006 | Halperin et al. | |
| 7,108,665 B2 | 9/2006 | Halperin et al. | |
| 7,118,542 B2 | 10/2006 | Palazzolo et al. | |
| 7,122,014 B2 | 10/2006 | Palazzolo et al. | |
| 7,149,579 B1 | 12/2006 | Koh et al. | |
| 7,177,684 B1 | 2/2007 | Kroll et al. | |
| 7,220,235 B2 | 5/2007 | Geheb et al. | |
| 7,277,752 B2 | 10/2007 | Matos | |
| 7,295,871 B2 | 11/2007 | Halperin et al. | |
| 7,340,296 B2 | 3/2008 | Stahmann et al. | |
| 7,427,921 B2 | 9/2008 | Van Woudenberg | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,702,390 B1 | 4/2010 | Min | |
| 7,810,172 B2 | 10/2010 | Williams | |
| 7,831,303 B2 | 11/2010 | Rueter et al. | |
| 7,974,689 B2 | 7/2011 | Volpe et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,369,944 B2 | 2/2013 | Macho et al. | |
| 8,600,486 B2 | 12/2013 | Kaib et al. | |
| 8,649,861 B2 | 2/2014 | Donnelly et al. | |
| 8,706,215 B2 | 4/2014 | Kaib et al. | |
| 8,904,214 B2 | 12/2014 | Volpe et al. | |
| 8,909,335 B2 | 12/2014 | Radzelovage | |
| 9,008,801 B2 | 4/2015 | Kaib et al. | |
| 9,135,398 B2 | 9/2015 | Kaib et al. | |
| 2002/0107435 A1 | 8/2002 | Swetlik et al. | |
| 2003/0004547 A1 | 1/2003 | Owen et al. | |
| 2003/0023277 A1 | 1/2003 | Owen et al. | |
| 2003/0032988 A1 | 2/2003 | Fincke | |
| 2003/0055460 A1 | 3/2003 | Owen et al. | |
| 2003/0095648 A1 | 5/2003 | Kaib et al. | |
| 2003/0149462 A1 | 8/2003 | White et al. | |

(56) References Cited

U.S. PATENT DOCUMENTS

| | | |
|---|---|---|
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0233129 A1* | 12/2003 | Matos ............... A61B 5/0006 607/5 |
| 2004/0007970 A1 | 1/2004 | Ma et al. |
| 2004/0049233 A1 | 3/2004 | Edwards |
| 2004/0143297 A1 | 7/2004 | Ramsey |
| 2005/0049515 A1 | 3/2005 | Misczynski et al. |
| 2005/0131465 A1 | 6/2005 | Freeman et al. |
| 2006/0017575 A1* | 1/2006 | McAdams ........... A61B 5/0031 340/573.1 |
| 2006/0036292 A1 | 2/2006 | Smith et al. |
| 2006/0085049 A1 | 4/2006 | Cory et al. |
| 2006/0129067 A1* | 6/2006 | Grajales ............. A61B 5/6804 600/586 |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2007/0299474 A1 | 12/2007 | Brink |
| 2008/0004536 A1 | 1/2008 | Baxi et al. |
| 2008/0015454 A1 | 1/2008 | Gal |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0221631 A1 | 9/2008 | Dupelle |
| 2008/0249591 A1 | 10/2008 | Gaw et al. |
| 2008/0287770 A1 | 11/2008 | Kurzweil et al. |
| 2008/0306560 A1 | 12/2008 | Macho et al. |
| 2008/0306562 A1 | 12/2008 | Donnelly et al. |
| 2008/0312520 A1 | 12/2008 | Rowlandson et al. |
| 2008/0312709 A1 | 12/2008 | Volpe et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082691 A1 | 3/2009 | Denison et al. |
| 2009/0093687 A1 | 4/2009 | Telfort et al. |
| 2009/0138059 A1 | 5/2009 | Ouwerkerk |
| 2009/0177100 A1 | 7/2009 | Ternes |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0083968 A1 | 4/2010 | Wondka et al. |
| 2010/0179438 A1 | 7/2010 | Heneghan et al. |
| 2010/0234715 A1 | 9/2010 | Shin et al. |
| 2010/0234716 A1 | 9/2010 | Engel |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0077728 A1 | 3/2011 | Li et al. |
| 2011/0196220 A1 | 8/2011 | Storm |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0150008 A1 | 6/2012 | Kaib et al. |
| 2012/0158074 A1 | 6/2012 | Hall |
| 2012/0158075 A1 | 6/2012 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0371806 A1 | 12/2014 | Raymond et al. |
| 2015/0005588 A1 | 1/2015 | Herken et al. |
| 2015/0039053 A1 | 2/2015 | Kaib et al. |
| 2015/0217121 A1 | 8/2015 | Subramanian et al. |
| 2015/0231403 A1 | 8/2015 | Kaib et al. |
| 2016/0143585 A1 | 5/2016 | Donnelly et al. |

FOREIGN PATENT DOCUMENTS

| | | |
|---|---|---|
| EP | 0295497 B1 | 9/1993 |
| EP | 0335356 B1 | 3/1996 |
| EP | 1642616 A2 | 4/2006 |
| EP | 1455640 B1 | 1/2008 |
| EP | 1720446 B1 | 7/2010 |
| JP | S6368135 A | 3/1988 |
| JP | 5115450 A | 5/1993 |
| JP | H10-28679 A | 2/1998 |
| JP | H11319119 A | 11/1999 |
| JP | 2002-102361 A | 4/2002 |
| JP | 2002-514107 A | 5/2002 |
| JP | 2002200059 A | 7/2002 |
| JP | 2002534231 A | 10/2002 |
| JP | 2003235997 A | 8/2003 |
| JP | 2004538066 A | 12/2004 |
| JP | 2005275606 A | 10/2005 |
| JP | 2007531592 A | 11/2007 |
| JP | 2008302228 A | 12/2008 |
| JP | 2009510276 A | 3/2009 |
| JP | 2009518057 A | 5/2009 |
| JP | 2009528909 A | 8/2009 |
| JP | 2010-508128 A | 3/2010 |
| JP | 2010530114 A | 9/2010 |
| WO | 200002484 A1 | 1/2000 |
| WO | 2004054656 A1 | 7/2004 |
| WO | 2005082454 A1 | 9/2005 |
| WO | 2006050235 A1 | 5/2006 |
| WO | 2007019325 A2 | 2/2007 |
| WO | 20070057169 A1 | 5/2007 |
| WO | 2007077997 A1 | 7/2007 |
| WO | 2008137286 A1 | 11/2008 |
| WO | 2009034506 A1 | 3/2009 |
| WO | 2010014497 A1 | 2/2010 |
| WO | 2010025432 A1 | 3/2010 |

OTHER PUBLICATIONS

DeBock et al., "Captopril treatment of chronic heart failure in the very old," J. Gerontol. (1994) 49: M148-M152.

Extended European Search Report from corresponding European Application No. 11804401.5 dated May 18, 2016.

Harnett, P.R. et al., "A Survey and Comparison of Laboratory Test Methods for Measuring Wicking", Textile Research Journal, Jul. 1984.

International Search Report dated Nov. 21, 2011 from corresponding International Application No. PCT/US11/43360.

(56) References Cited

OTHER PUBLICATIONS

O'Keeffe et al., "Reproducability and responsiveness of quality of life assessment and six minute walk test in elderly heart failure patients," Heart (1998) 80: 377-382.

O'Keeffe et al., "Reproducability and responsiveness of quality of the assessment and six minute walk test in elderly heart failure patients," Heart (1998) 80: 377-382.

* cited by examiner

WEARABLE MEDICAL MONITORING DEVICE

CROSS-REFERENCE TO RELATED APPLICATIONS

This application is a Continuation of U.S. patent application Ser. No. 15/010,778, titled "Wearable Medical Monitoring Device," filed on Jan. 29, 2016, which is incorporated herein by reference in its entirety. U.S. patent application Ser. No. 15/010,778 is a Continuation of U.S. patent application Ser. No. 14/175,433 (now U.S. Pat. No. 9,283,399), titled "Wearable Medical Treatment Device," filed on Feb. 7, 2014, which is incorporated herein by reference in its entirety. U.S. patent application Ser. No. 14/175,433 is a Continuation of U.S. patent application Ser. No. 13/416,734 (now U.S. Pat. No. 8,649,861), titled "Wearable Medical Treatment Device," filed on Mar. 9, 2012, which is incorporated herein by reference in its entirety. U.S. patent application Ser. No. 13/416,734 is a Continuation of U.S. patent application Ser. No. 12/833,173 (now U.S. Pat. No. 8,140,154), titled "Wearable Medical Treatment Device," filed on Jul. 9, 2010, which is incorporated herein by reference in its entirety. U.S. patent application Ser. No. 12/833,173 is a Continuation-in-part of, and claims priority to U.S. patent application Ser. No. 12/002,469 (now U.S. Pat. No. 7,974,689), titled "Wearable Medical Treatment Device with Motion/Position Detection," filed on Dec. 17, 2007, which is incorporated herein by reference in its entirety. U.S. patent application Ser. No. 12/002,469 claims priority under 35 U.S.C. § 119(e) to U.S. Patent Application No. 60/934,404, titled "Wearable Medical Treatment Device with Motion/Position Detection," filed on Jun. 13, 2007. This application further incorporates by reference, in their entireties, U.S. Pat. Nos. 4,928,690; 6,065,154; 5,944,669; 5,741,306; 6,681,003; 6,253,099; and 5,078,134.

BACKGROUND OF THE INVENTION

1. Field of Invention

At least one embodiment of the present invention relates generally to a wearable therapeutic device, and more specifically, to a wearable therapeutic device configured to monitor or treat a subject.

2. Discussion of Related Art

Heart failure and other chronic conditions are a major health concern worldwide. Heart failure is a progressive disease with varying symptoms such as fatigue, coughing, diminished exercise capacity, shortness of breath, fluid retention, swelling in the abdomen or legs, lung congestion, and cardiac arrhythmias. Heart failure can be treated, and its symptoms mitigated, by lifestyle modifications, medications, surgical procedures such as heart transplants, and mechanical therapies. These efforts can come with side effects and limited success rates. Heart failure continues to reduce the quality of life of victims.

SUMMARY OF THE INVENTION

Aspects and embodiments of the present invention are directed to a wearable therapeutic and monitoring treatment device. The device monitors and collects health related information from the subject, and uses this information to determine if treatment is warranted, to suggest lifestyle modifications, and to adjust treatment regimens. The device can further include an external defibrillator to apply treatment such as defibrillation to the subject when necessary. By monitoring a subject's conditions in a nearly continuous fashion in essentially real time, a comprehensive medical record of the subject can also be developed on a long term basis, for further treatment and analysis.

At least one aspect is directed to a wearable treatment device. The treatment device includes a cardiac sensing electrode, a treatment electrode, a user interface, and a sensor. The cardiac sensing electrode can be positioned outside a body of the subject and can detect cardiac information. The treatment electrode can be positioned outside the body of the subject and can apply treatment to the subject. The user interface can receive quality of life information from the subject. The sensor can be positioned outside the body of the subject and can detect subject activity and wellness information indicative of a general wellness of the subject. The treatment device also includes a controller. The controller can communicatively couple to the cardiac sensing electrode, the treatment electrode, the user interface, and the sensor. The controller receives the detected cardiac information, the quality of life information, and the detected subject activity and wellness information, and determines that treatment is to be applied to the body of the subject based upon the detected cardiac information. The controller can also adjust the treatment based on at least one of the detected subject activity and wellness information and the quality of life information. The treatment device can also include an alarm module to provide an alarm after the cardiac information is detected and before the treatment is applied to the body of the subject.

At least one other aspect is directed to a method of facilitating care of a subject. The method includes acts of sensing cardiac information of the subject, sensing subject activity and wellness information of the subject, and receiving quality of life information from the subject. The method determines that treatment is to be applied to the subject based upon the cardiac information, and adjusts the treatment based on at least one of the detected subject activity and wellness information and the quality of life information. The method also alerts at least one of the subject, a rescuer, a bystander, and a health care provider of a treatment regimen subsequent to sensing the cardiac information, and applies the treatment to the subject subsequent to alerting at least one of the subject, the rescuer, the bystander, and the health care provider of the treatment regimen.

At least one other aspect is directed to a method of facilitating care of a subject. The method includes an act of providing a wearable treatment device. The wearable treatment device includes a cardiac sensing electrode and a treatment electrode. The wearable treatment device also includes a user interface to receive quality of life information from the subject, and a sensor to detect subject activity and wellness information indicative of a general wellness of the subject. The wearable treatment device also includes a controller. The controller can couple with the cardiac sensing electrode, the treatment electrode, the user interface, and the sensor, to receive the detected cardiac information, the quality of life information, and the detected subject activity and wellness information. The controller determines that treatment is to be applied to the body of the subject based upon the detected cardiac information. The treatment can be adjusted under the direction of the controller and based on at least one of the detected subject activity and wellness information and the quality of life information. An alarm module can provide an alarm after the cardiac information is detected and before the treatment is applied to the body of the subject.

In various embodiments, the alarm module can provide a second instance of the alarm after the treatment is applied to the body of the subject. The user interface can prevent application of the treatment to the body of the subject. In one embodiment, the treatment device includes a second sensor. The second sensor can be positioned outside the body of the subject and can detect subject activity and wellness information. The controller can determine that the treatment device is properly positioned on the subject based at least in part on a position of the first sensor and a position of the second sensor.

In some embodiments, the controller can provide at least one of the cardiac information and the subject activity and wellness information to a computer server via a network. The controller can also generate a report based on the cardiac information and the subject activity and wellness information. The report may suggest a change in at least one of a treatment regimen, an exercise regimen, and a diet regimen.

In various embodiments, a wearable treatment device is provided that includes a cardiac sensing electrode, a treatment electrode, a user interface, a sensor; and a controller. The cardiac sensing electrode and the treatment electrode are positioned outside the subject. The sensor is positioned to detect the subject activity and wellness information of the subject, and the user interface receives the quality of life information. In some embodiments, the wearable treatment device substantially continuously senses at least one of cardiac information and subject activity and wellness information, and provides at least one of the cardiac information and the subject activity and wellness information to a computer server via a network. The wearable treatment device can also generate a report based on the cardiac information and the subject activity and wellness information, or suggest a change in at least one of a treatment regimen, an exercise regimen, and a diet regimen.

In some embodiments, instructions are provided to operate the wearable treatment device. The instructions include at least one instruction to position at least one of the cardiac sensing electrode and the sensor on the subject. The instructions can also include at least one instruction to position the wearable treatment device on the subject.

In one aspect of the present invention, a wearable monitoring device is provided comprising a plurality of cardiac sensing electrodes configured to be positioned outside a body of a subject and to detect cardiac information of the subject, a monitor configured to administer a predetermined test to the subject and having a user interface configured to receive quality of life information from the subject, at least one motion sensor configured to be positioned outside the body of the subject and to detect subject motion during the predetermined test, and a controller communicatively coupled to the plurality of cardiac sensing electrodes, the monitor, and the at least one motion sensor, the controller configured to receive and store the detected cardiac information, the quality of life information, and the detected subject motion, and to communicate the stored detected subject motion and the quality of life information to a remote computer. In one embodiment, the quality of life information identifies at least one of a fatigue level and a breathing level of the subject. In another embodiment, the quality of life information identifies information about at least one of the subject's lifestyle, body weight, blood pressure, eating and exercise habits, symptom information, fatigue information, breathing level and how the subject currently feels. In an alternative embodiment, the predetermined test is a six minute walk test.

In another embodiment, the at least one motion sensor includes at least one accelerometer. In one embodiment, the controller determines a distance travelled by the subject during the six minute walk test based upon the detected subject motion from the at least one accelerometer. In one embodiment, the device further comprises at least one additional sensor communicatively coupled to the controller to detect at least one of blood pressure, blood oxygen level, respiration, and temperature. In one embodiment, the controller wirelessly communicates the stored detected subject motion and the quality of life information to the remote computer. In another embodiment, the at least one motion sensor includes a pedometer, and the controller determines a distance travelled by the subject during the six minute walk test based upon the detected subject motion from the pedometer.

In one embodiment, the monitoring device further comprises at least one additional sensor communicatively coupled to the controller to detect at least one of blood pressure, blood oxygen level, respiration, hypovolemia, and temperature. In one embodiment, the quality of life information further includes information about at least one of the subject's lifestyle, body weight, blood pressure, eating and exercise habits, symptom information, fatigue information, and how the subject currently feels. In one embodiment, the predetermined test is a six minute walk test, and wherein the at least one motion sensor includes at least one accelerometer. In an alternative embodiment, the device further comprises at least one additional sensor communicatively coupled to the controller to detect at least one of blood pressure, blood oxygen level, respiration, hypovolemia, and temperature. In yet another embodiment, the predetermined test is a six minute walk test, and wherein the at least one motion sensor includes a pedometer.

In one embodiment, the predetermined test is a six minute walk test, and the at least one motion sensor includes at least one of an accelerometer and a pedometer. In one embodiment, the user interface is configured to guide the subject through the predetermined test. In one embodiment, the device further comprises at least one additional sensor communicatively coupled to the controller to detect at least one of blood pressure, blood oxygen level, respiration, hypovolemia, and temperature. In another embodiment, the quality of life information identifies a fatigue level and a breathing level of the subject.

In one embodiment, the quality of life information is received from the subject in response to questions posed to the subject via the user interface of the monitor. In one embodiment, the quality of life information is received from the subject in response to questions posed to the subject via the user interface of the monitor. In one embodiment, the questions are posed to the subject at selectable intervals. In another embodiment, the user interface is configured to guide the subject through the predetermined test. In an alternative embodiment, the user interface is configured to prompt the subject to perform the predetermined test.

In one embodiment, the user interface is configured to prompt the subject to provide the quality of life information. In one embodiment, the device comprises at least one additional sensor communicatively coupled to the controller to detect the subject's body position. In one embodiment, the device comprises detecting the subject's body position in one of an upright position and a prone position, and detecting that the subject is asleep. In another embodiment, the device further comprises at least one additional sensor communicatively coupled to the controller to detect at least one of sleep apnea, wheezing, and coughing.

In an alternative embodiment, the monitoring device comprises at least one additional sensor communicatively coupled to the controller to measure impedance of the subject's thoracic cavity. In one embodiment, the quality of life information identifies compliance with a prescribed treatment. In another embodiment, the quality of life information identifies nutritional content of a food item, wherein the user interface further comprises a bar code scanner configured to scan a bar code of a food item, and wherein the controller is further configured to access information about the nutritional content of the food item with reference to the bar code.

Other aspects, embodiments, and advantages of these exemplary aspects and embodiments are discussed in detail below. Both the foregoing information and the following detailed description are illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
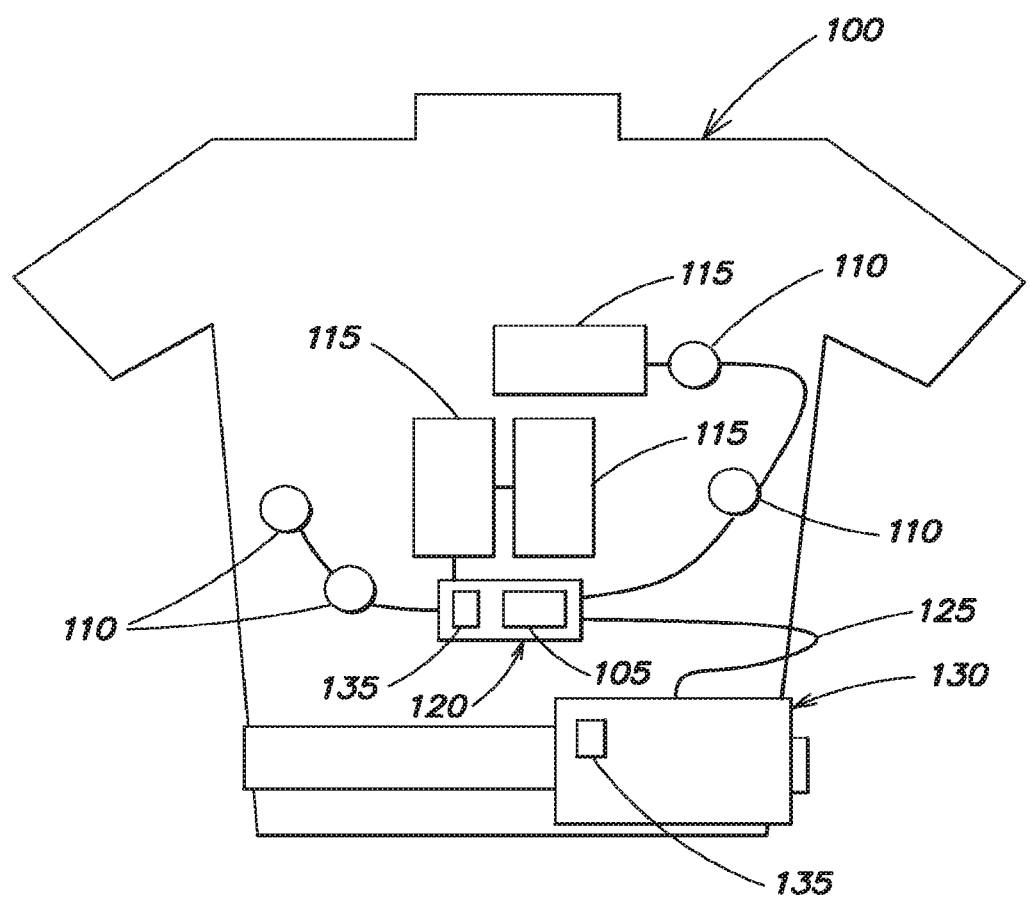
FIG. 1 depicts a diagrammatic representation of treatment device positioning on a subject in accordance with an embodiment.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Various aspects and embodiments are directed to a wearable treatment device that senses information about a subject's condition. This information includes cardiac information, subject activity and wellness information, and subject quality of life information. This information can be aggregated into reports on the subject's condition that can be used to provide or adjust treatment regimens. An alarm module can indicate that treatment has been, is being, or will be applied.

FIG. 1 illustrates wearable treatment device 100 configured for a subject to wear as a garment. The subject includes a person receiving health care, such as a subject who may or may not be under supervision of a doctor or health care provider. The subject may be in or out of a hospital setting, and the subject can engage in day to day life activities, at home, work, leisure, and play while wearing treatment device 100. Treatment device 100 includes monitoring, treatment and data transmission and processing capability, and can be worn as a vest, belt, shirt, or series of straps, garment, or undergarment for example. Treatment device 100 may include at least one power supply such as a battery, or other power supplies, including AC power supplies and uninterruptable power supplies. Treatment device 100 can monitor and treat cardiac ailments such as heart failure, as well as other medical conditions such as arrhythmias, pulmonary ailments, other heart irregularities, sleep disorders, and circulatory system deficiencies such as blockages.

In one embodiment, treatment device 100 includes dedicated control logic devices that collectively constitute a control system, such as at least one controller 105. Controller 105 can include programmable logic devices and arrays, application specific integrated circuits, hardware and software combinations, general purpose processors and dedicated controllers, for example. Further, treatment device 100 may include graphical user interfaces or other interfaces to provide output information and receive input information from a user. Controller 105 can be contained entirely within treatment device 100, or at least partially located external to treatment device 100, such as at a remote computer server in a doctor's office, data center, or other location. In one embodiment, controller 100 includes at least one processor as described in commonly owned U.S. patent application Ser. No. 12/833,096, entitled "System and Method for Conserving Power in a Medical Device," filed on Jul. 9, 2010, which is incorporated by reference herein in its entirety. The referenced application generally discloses a processing architecture configured to conserve energy.

Treatment device 100 can also include a plurality of sensors 110, 135. The plurality of sensors 110, 135 may include subject medical condition sensors 110, such as cardiac sensing electrodes, and subject activity sensors 135, such as motion sensors or accelerometers. While four external medical condition sensors 110 are illustrated in FIG. 1, treatment device 100 can include more or less than four external medical condition sensors 110, and in some embodiments, sensors 110 include at least one internal sensor or external dry electrode. Sensors 110 may include at least one cardiac sensing electrode to detect a subject's cardiac information related to the subject's heartbeat or electrical activity of the subject's heart. Sensors 110 are configured for placement proximate to the subject, for example, about the subjects torso, chest, back, limbs, or neck, where they can sense information about the subject's bodily functions. In one embodiment, sensors 110 include a fingertip pulse oximeter that can generate a photoplethysmograph to measure blood flow, blood oxygen saturation, respiration, or hypovolemia. In other embodiments, sensors 110 can include sensors that monitor or measure wellness information indicative of a general wellness of the subject, such as pulse, breathing, temperature, blood pressure, or fatigue information, for example.

In one embodiment, the plurality of sensors 110, 135 includes subject activity sensors 135. In one embodiment, subject activity sensors 135 can include at least one accelerometer to detect subject movement, lack thereof, or positional orientation. Sensors 110, 135 that include subject activity sensors generally detect tangible medical or physical condition or information indicative of a subject's overall health, as well as statistically significant changes in measurements or conditions with time that may indicate changes in the subject's health, such as a worsening heart failure condition.

Treatment device 100 may also include at least one treatment electrode 115. In one embodiment, treatment electrode 115 is configured to deliver shocks or electric current to the subject, such as a defibrillation shock applied to resuscitate a subject during cardiac arrest or another cardiac event. Treatment electrodes 115 may be housed in therapy pads that also include receptacles to house conductive fluid such as conductive gel. For example, treatment electrodes 115 may include dry treatment electrodes. In this example, prior to treatment, controller 105 can direct the receptacle to burst, releasing conductive fluid that contacts a surface of treatment electrode 115 as well as the subject's skin, enhancing the electrical connection between the subject and treatment electrode 115. The receptacles can be replaced after use.

In one embodiment, treatment electrodes 115 are formed from plates of metal or other conductive material having a conductive surface and configured for contact with the subject. The therapy electrodes may have generally circular, oval, rectangular, square, or other geometric forms with a generally continuous surface. In some embodiments, treatment electrodes 115 are formed from conductive wire or thread sewn into treatment device 100 in stitched, woven, or intertwined patterns, including a mesh pattern. In one embodiment, treatment device 100 includes at least one node 120 to connect or interface with sensors 110 and treatment electrodes 115. Node 120 may be located on a belt of treatment device 100 and can be part of or associated with controller 105 to facilitate communication between controller 105, sensors 110, 135 and treatment electrodes 115. In one embodiment, node 120 is a device to physically couple cables 125 that connect controller 105, sensors 110, 135 treatment electrodes 115, and other treatment device 100 components, such as at least one monitor 130. FIG. 1 depicts three treatment electrodes 115, with one treatment electrode positioned proximate to the subject's chest, and two treatment electrodes 115 positioned proximate to the subject's back. This configuration can be used to provide shocks to the subject's heart during defibrillation treatment. Other configurations and positions of treatment electrodes 115 are possible for defibrillation and other treatments.

In one embodiment, treatment device 100 includes at least one subject activity sensor 135. For example, subject activity sensor 135 may include at least one accelerometer that can indicate accelerating and decelerating movements. For example, a subject wearing treatment device 100 can participate in normal activities, such as standing, walking, sitting, running, and generally moving about as part of day-to-day life when partaking in physical, labor, and leisure activities. Because of the nature of human movements, generally comprising short distance and short duration, accelerometers provide useful information about subject movement and activity. Controller 105 can use this information to determine if treatment is necessary or should be adjusted, if quality of life recommendations should be made to the subject (e.g., a suggestion to change dietary or activity habits) or if a doctor should be consulted. In some embodiments, activity sensors 135 include single axis accelerometers as well as multi-axis sensors.

In one embodiment, the plurality of sensors 110, 135 include at least one cardiac sensing electrode 110, a subject activity sensor 135, such as an accelerometer, or other sensor configured to provide information to controller 105 relating to the subjects cardiac information (e.g., ECG), or activity wellness (e.g., motion or position). For example, sensor 135 can sense and provide information about the subject's body state—e.g., vertical, horizontal, lying down on left side, lying down on right side, moving in a recitative pattern, vibrating due to environmental causes such as during a car ride, convulsing due to health causes such as a cardiac event or seizure, accelerating, decelerating, falling, and treatment device 100 component acceleration or mechanical shock, (e.g., sensor 135 disconnects from the subject and falls or impacts the ground or a hard surface due to gravitational or other forces).

In one embodiment, treatment device 100 includes two activity sensors 135, such as accelerometers. For example, a first accelerometer can be located on node 120 and a second accelerometer can be located on monitor 130. In one embodiment, the first accelerometer is positioned on the subject's upper body, and the second accelerometer 135 is positioned proximate to the subject's waist. Accelerometers or other activity sensors 135 may also be positioned on the subject's limbs. Activity sensors 135, including accelerometers, may include at least one position, force, or motion detector. In one embodiment, controller 105 uses information detected by multiple activity sensors 135, such as accelerometers to determine and predict subject activity, and to calibrate or verify the accuracy of sensors 110 and/or sensors 135. For example, one or more of sensors 110 may be tasked with determining the subject's heart beat, and may shift due to movement or be improperly positioned so that an inaccurate reduced heartbeat is sensed. In this example, activity sensors 135 may indicate that the subject is exercising and where an elevated heartbeat would be expected, while sensor 110 detects a reduced heart beat or no heart beat because it is improperly positioned on the subject. Controller 105 can identify this discrepancy and notify the subject, for example by a display on monitor 130, that one of sensors 110 should be repositioned. By processing sensed information and information received from the user, controller 105 may also determine that treatment device 100 components have been tampered with or damaged, and monitor 130 can display a notification of any such tampering or damage. In one embodiment, controller 105 is located together with monitor 130.

In one embodiment, controller 105 evaluates activity sensor 135 information to determine the position of the subject and any corresponding applied forces. For example, activity sensor 135 can measure x, y, and z axis orientations of the subject. Controller 105 can use this information in a confidence based arrhythmia detection algorithm to accelerate or delay the timing of treatment based on past and present body motion or position history. Multiple activity sensors 135 permit separate evaluation of different subject movements and controller 105 evaluates subject movements to determine subject activity, create a real time and comprehensive subject medical record, and to recommend, apply, or adjust treatment regimens. The treatment applied can depend upon the diagnostic requirement of the subject's doctor and the condition of the subject (e.g., heart failure or congestive heart failure) that the doctor or the subject wishes to monitor.

In one embodiment, activity sensors 135 include at least one accelerometer to sense high sensitivity subject activity and wellness information, such as breathing or other generally subtle forms of motion such as body position (e.g., standing or prone). Sensors 110, 135 can detect and monitor physical activity and activity trends, body positions, and sleep conditions, such as sleep apnea. For example, sleep apnea may be deduced based on pulse oximetry and respiration measurements. Sensors 135 can also include at least one accelerometer to measure low sensitivity data such as mechanical shock.

In some embodiments, activity sensors 135 include at least one multi-axis accelerometer, or two three-axis accelerometers with one of the accelerometers mounted on a vest portion of treatment device 100 and another of the accelerometers mounted elsewhere on treatment device 100, such as a strap about the waist, or on monitor 130, which can include a visual display where the orientation of the visual display is controlled by the output of accelerometer.

In one embodiment, treatment device 100 includes at least one monitor 130, which can include at least one touch screen, buttons, or other user interface such as a keyboard. The user interface may have multilingual audio and visual displays. Monitor 130 can also be remote from treatment device 100. Monitor 130 can display information to indicate that treatment device 100 is or is not properly configured about the subject. For example, monitor 130 can indicate that sensors 110, 135 are properly positioned and operational. Monitor 130 can attach to a belt or other portion of treatment device 100. In one embodiment, monitor 130 can be exposed, external to the subject's clothing, with at least some other treatment device components (e.g., sensors 110, 135) concealed beneath the subject's clothing. In one embodiment, treatment device 100 includes two monitors 130, with a first monitor housed on treatment device 100, and a second monitor remote to treatment device 100. The second monitor can communicate with controller 105. In one embodiment, the second monitor displays additional information that the first monitor does not display. For example, the second monitor can be part of a base station or a battery charger that includes a processor and memory. The second monitor can also be a personal computer monitor, (e.g., laptop, desktop, tablet, or mobile telephone monitor) configured to display the subject's historical medical record and other long term non-critical information, and the first monitor can be a dedicated application specific monitor that is housed on a belt of treatment device 100 configured to input and output core data related to the subject's present cardiac condition, general wellness, quality of life, and treatment regimen.

In one embodiment, monitor 130 displays medication reminders to prompt the subject to take medication. For example, monitor 130 can display visual information (that can be supplemented with audio information) telling the subject what medication to take, and when. In one embodiment, monitor 130 shows the subject what the medication (e.g., a pill) looks like (for example, by color, shape, markings, etc.), and issues a verbal prompt to remind the subject to take a certain medication and a certain time. After taking the medication, the subject can inform treatment device of this fact via a user interface of monitor 130.

Monitor 130 may also include an alarm module. The alarm module can be audio, visual, tactile, or haptic, and can alert the subject as well as bystanders that treatment device 100 has applied, is applying, or will apply electric current or other treatment to the subject. The alarm module can also provide indicators of the subject's condition, such as heart or respiration rates, volume, or timing, or the subject's pulse, as well as heart failure indicators and coronary sounds.

In one embodiment, the alarm module provides an alarm after sensor 110 detects cardiac information about the subject, and before treatment device 100 applies treatment to the subject. The alarm module can also provide a further alarm after treatment has been applied to the subject. For example, the alarm module can alert first responders that at least one defibrillation shock has already been applied by treatment device 100. The alarm module can also alert bystanders or rescuers that it is safe to contact the subject after treatment has been applied, or that another round of treatment (e.g., another shock) is forthcoming. In one embodiment, the alarm module indicates that treatment will be applied. When the subject does nothing to abort the forthcoming treatment (such as depressing an abort switch or entering instructions via the user interface) controller 105 can instruct treatment device 100 to administer an electric shock to the subject via one of treatment electrodes 115.

In FIG. 1, a first activity sensor 135 such as an accelerometer is located in front of the subject, for example attached to monitor 130, and a second activity sensor 135, such as an accelerometer is located in back of the subject, for example attached to a belt of treatment device 100. Other configurations of accelerometers are possible, in front, in back, and on the sides of the subject, and attached to different belts, straps, or other components of treatment device 100. Wire 125 allows communication and data transfer between activity sensor 135, medical condition sensors 110, and controller 105 via node 120.

Figure 2:
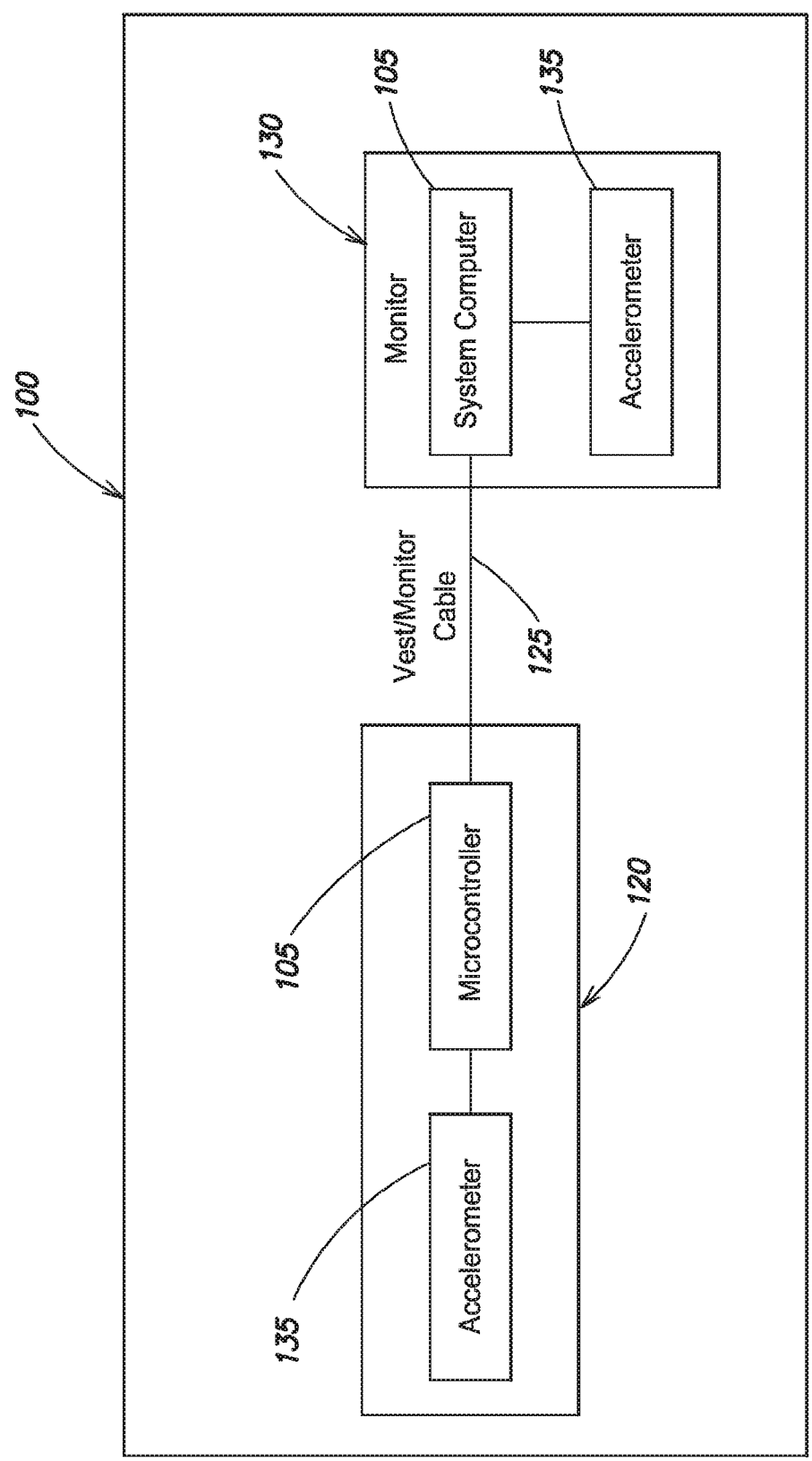
FIG. 2 depicts a block diagram of a treatment device in accordance with an embodiment.

FIG. 2 depicts a block diagram of treatment device 100. As illustrated in FIG. 2, controller 105 includes a microcontroller and a system computer, with the microcontroller associated with node 120 and the system computer associated with monitor 130, and with wire 125 connecting the microcontroller with the system computer. Different configurations are possible. For example, more than one logic device can collectively constitute controller 105, and controller 105 may be part of treatment device 100. In one embodiment, at least some logic devices of controller 105, such as the system computer, are located external to treatment device 100. For example, both monitor 130 and the system computer can be separate from treatment device 100. Such external components may communicate with the microcontroller or other elements of controller 105 that are part of or housed on treatment device 100 via wire 125 or other connections, both wired and wireless. In one embodiment, the microcontroller process real time information related to the subject's cardiac information, quality of life, general wellness, and treatment regimen; and the system computer processes information related to the subject's long term medical history. For example, controller 105 can provide information to a remote computer via a wireless transmission to generate a comprehensive real time medical history of the subject when, for example, the subject wears treatment device 100 for any period of time. This medical history information may be stored in memory that is part of treatment device 100, or remotely, for example in a hard drive of a computer in a doctor's office. The system computer and the microcontroller can exchange information and instructions regarding treatment application and adjustment. In one embodiment, controller 105 communicates a message to a physician, responder, bystander or the subject to indicate that treatment is imminent, being provided, or has already been provided.

In one embodiment, controller 105 communicates with a central server that is external to treatment device 100. For example, sensed indicators of heart failure can be wired or wirelessly downloaded to a central server for processing, and presented to a doctor for review and analysis. This information can be tailored to a doctor's needs, for example to generate alerts and notifications. With respect to data gathering, reference is made to U.S. Pat. No. 6,681,003, entitled "Data Collection and System Management for Patient-Worn Medical Devices," filed on Jul. 16, 2002, which is assigned to the assignee of the present application and incorporated herein by reference in its entirety. The referenced application generally discloses remote transmission and collection of data received from patient-worn medical devices.

In one embodiment, a first activity sensor 135, such as an accelerometer, is attached to node 120 and a second activity sensor 135, such as another accelerometer, is attached to monitor 130. Sensed information from both of these sensors 135 can be transferred to controller 105, which can be physically attached to treatment device 100, or remote from treatment device 100. In one embodiment, treatment device 100 includes two accelerometers to determine parameters such as subject body position, body movement, and body acceleration, and to perform self-diagnostics. Monitor 130 can contain either a high-G or a low-G accelerometer, or both. In one embodiment, a high-G low-sensitivity accelerometer can detect subject and equipment physical shock to determine if treatment device 100 is damaged. Activity sensors 135 can detect movement and orientation of the subject. In one embodiment, controller 105 processes information from two activity sensors 135, such as accelerometers 135 to identify subject activity. Processing of accelerometer data can be performed by the microcontroller or the system computer. Accelerometers can indicate change in the subject's velocity. For example, the subject can have an activity level when conscious that includes changes in both velocity and direction. By contrast, an unconscious subject may have little or no change in body motion. Other activity sensors 135 (e.g., gyroscope, magnetometer, hall-effect devices, pedometers, global positioning systems, and other force motion or position sensors) can indicate motion or lack of motion. Outputs from sensors 135 may be integrated, compared or differentiated by controller 105 to predict subject activity, and reduce interference or error signals.

Figure 3:
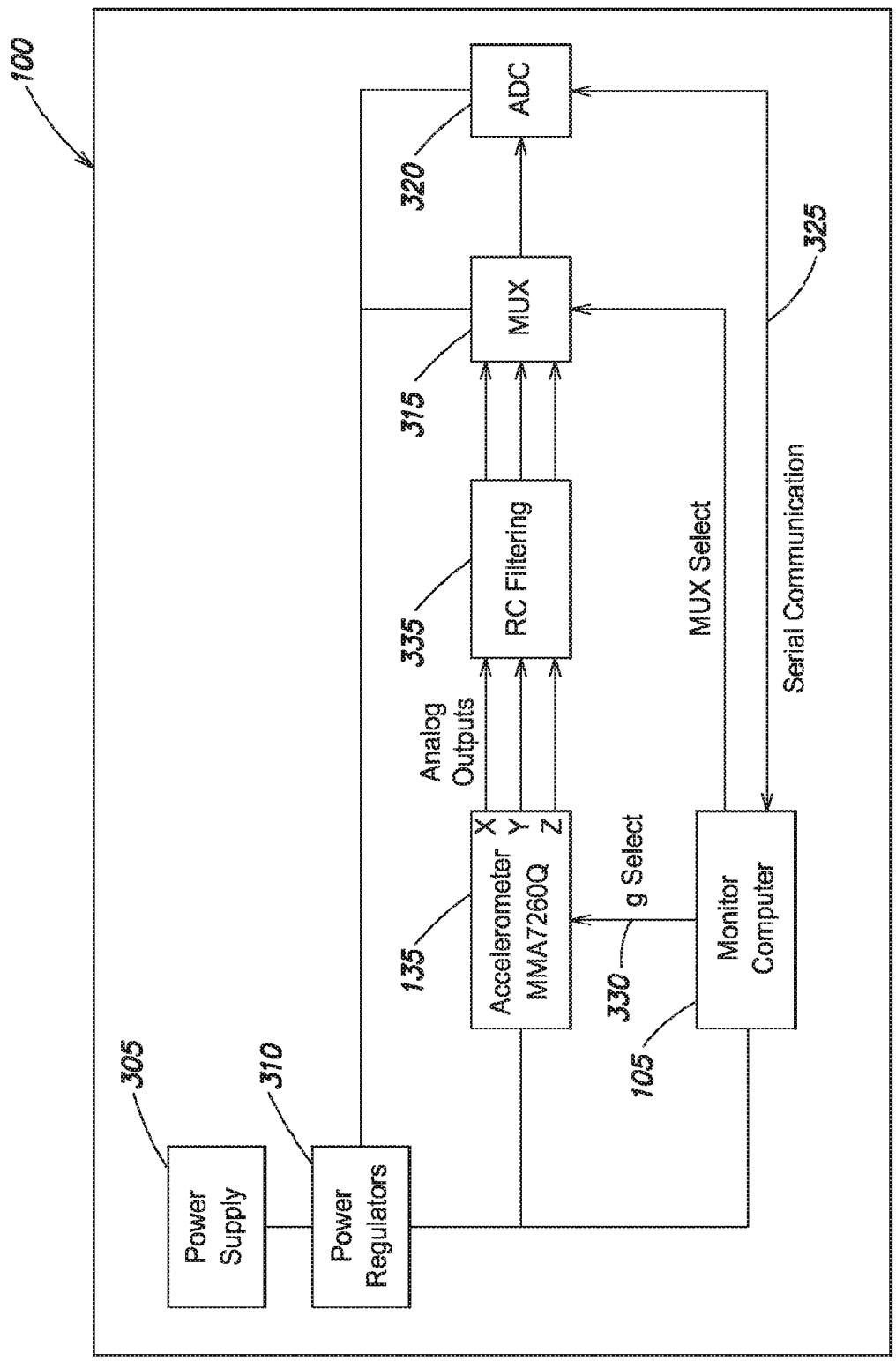
FIG. 3 depicts a block diagram of a treatment device in accordance with an embodiment.

FIG. 3 depicts a block diagram of a treatment device 100. In one embodiment, AC or DC power supply 305 (e.g., a power cord to AC main lines, or a battery) can power treatment device 100 components, such as controller 105, monitor 130, and sensors 110, 135. At least one power regulator 310 can control the power from power supply 305.

In one embodiment, controller 105 controls various system parameters such as activity sensor sensitivity, multiplexer (MUX) 315 channel select, the analog to digital converter (ADC) 320, and serial communication with controller 105 via serial communication bus 325 to acquire data from activity sensors 135 and to display this information at monitor 130. MUX 315 and ADC 320 can be internal to controller 105, or can be separate components. In one embodiment, activity sensors 135 include a Freescale Semiconductor MMA7260Q three axis low-g micromachined accelerometer. The g-select control line 330 coupled to controller 105 and the accelerometer allows the sensitivity to be varied from, for example, 1.5 g to 6 g. A high-G low sensitivity accelerometer can also be used to allow subject/equipment shock to be detected. Resistor-capacitor (RC) filter 335 can connect to outputs of the accelerometer to minimize clock noise from the accelerometer internal switched capacitor filter circuit. Controller 105 can control select lines of multiplexor 315 and may allow each axis output of the accelerometer to be switched to the Analog to Digital Converter (ADC) 320 input. Controller 105 can also control ADC 320 via a serial interface. In one embodiment, sensors 110, 135, controller 105, and monitor 130 sense, process, and display other information such as sensed cardiac information, sensed general wellness information, and subject inputted self assessment entries including quality of life information.

Figure 4:
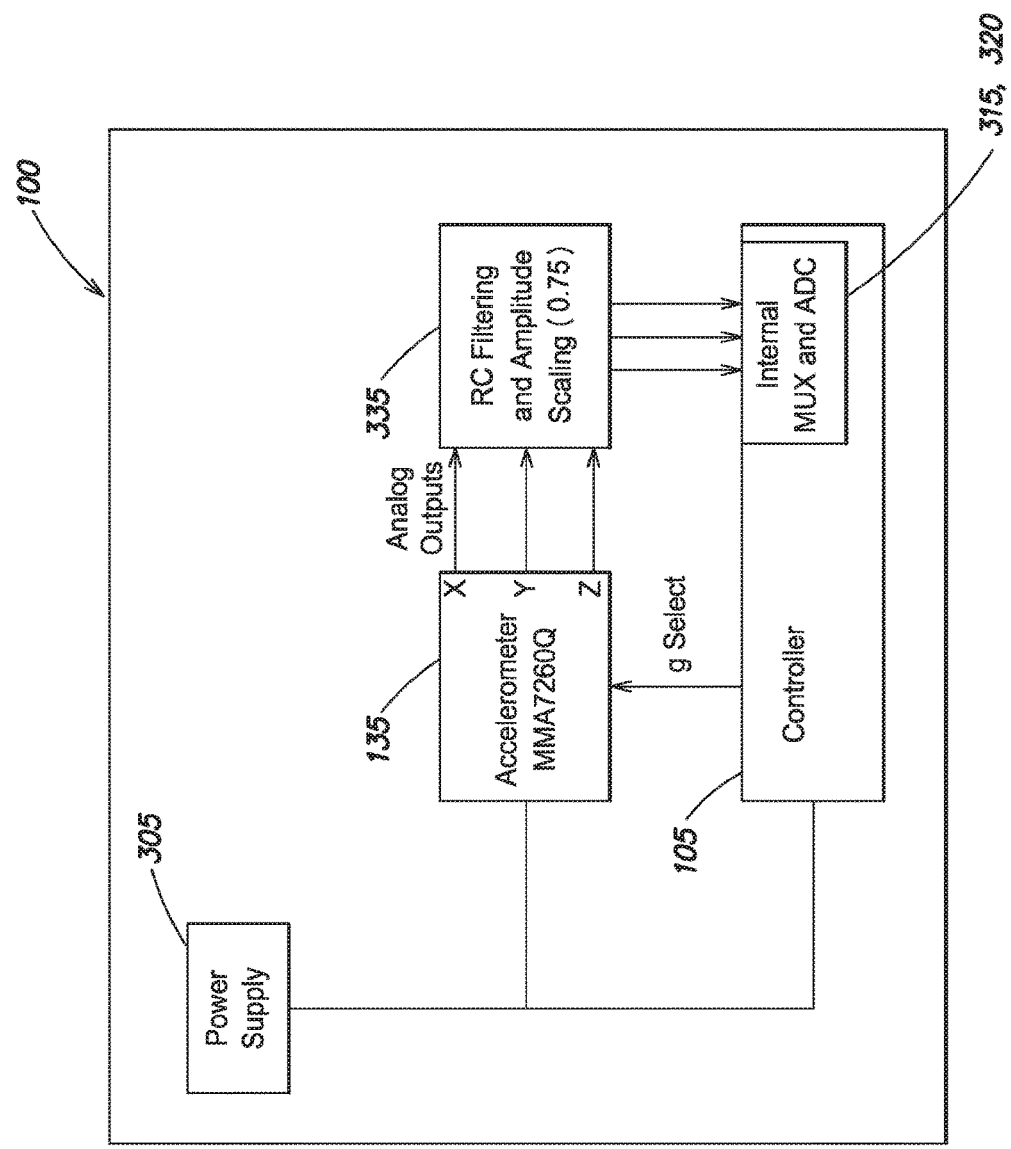
FIG. 4 depicts a block diagram of a treatment device in accordance with an embodiment.

FIG. 4 depicts an alternative block diagram of a treatment device 100 where controller 105 acquires information from activity sensor 135, such as an accelerometer. Power supply 305 can be used to power the components of treatment device 100. Activity sensor 135 can include a Freescale Semiconductor MMA7260Q three axis low-g micromachined accelerometer. Controller 105 controls the g-select lines that again can allow the sensitivity to be varied from, for example, 1.5 g to 6 g. RC filter 335 as well as amplitude scaling can be applied to each of the accelerometer outputs. In one embodiment, MUX 315 and ADC 320 are internal to controller 105 the analog outputs of the accelerometer are interfaced digitally directly to the controller 105.

In one embodiment, controller 105 detects an arrhythmia by assigning various confidence coefficients or weighting values to the various sensors 110, 135) that communicate with controller 105. In one embodiment, this is done prior to controller 105 determining a confidence level that detected motion indicates true motion, and not a false positive motion indication due, for example, to an incorrectly placed or dropped activity sensor 135. For example, controller 105 can separately analyze two independent ECG data streams from sensors 110 to extract heart rate, morphology, frequency information, general wellness, and other information. Controller 105 can perform additional analysis, independently on each channel, to analyze the signal for noise contamination that may result from subject motion or biological signals such as muscle noise. Secondary inputs to the basic detection algorithm can include a subject response button or override switch, where for example the subject indicates that they are in motion, and inputs from activity sensors 135. In one embodiment, controller 105 determines that the lack of response from the subject, for example, by not pressing a subject response button (e.g., an abort switch) that can be part of treatment device 100, means that the subject is unconscious.

In one embodiment, a weighting value is assigned to each sensor 110, 135 and the response button to make the decision that a treatable arrhythmia condition exists. In addition, the weighting values can be used to manipulate or adjust the timing and nature of therapy delivered by therapy electrodes 115.

During use by a subject, there may be instances where a first ECG channel contains noise and a second ECG channel is clean. For example two pairs of sensors 110 can independently obtain ECG signals, with one pair being contaminated with artifacts and the other being clean. The two ECG signals can be obtained simultaneously or sequentially, and can be transmitted to controller 105 via the same or different communication channels (e.g., wire 125). In one embodiment, controller 105 places more weight on the clean ECG channel. For example, to enhance a confidence level of the sensed information, a weighting can be assigned that would delay delivery of treatment by treatment electrodes 115 while sensors 135 and controller 105 determine if there is subject motion.

Figure 5:
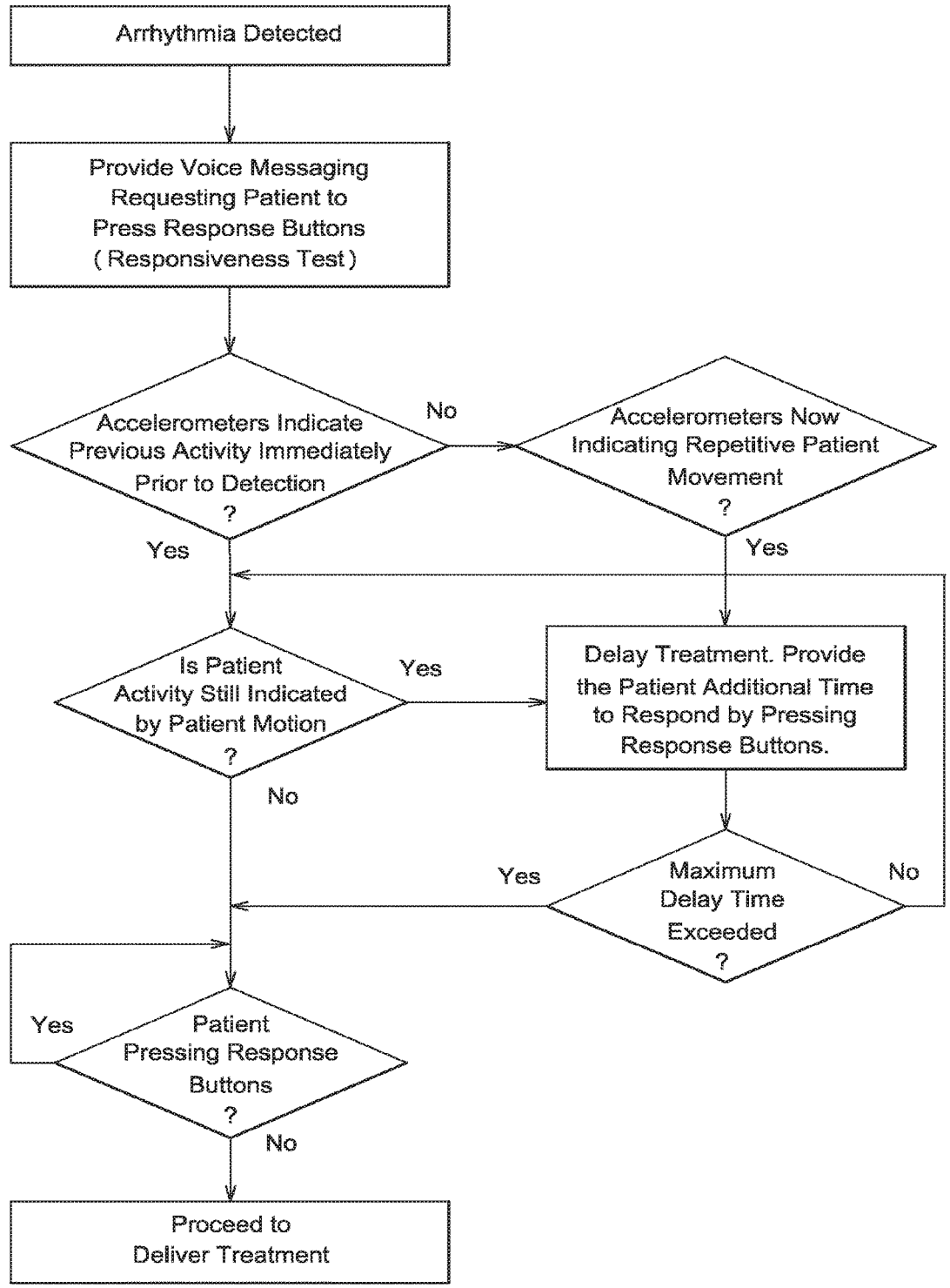
FIG. 5 depicts a flow chart for a method of monitoring and treating a subject in accordance with an embodiment.

The flow diagram in FIG. 5 shows that if subject motion is detected prior to the detection of a treatable arrhythmia, the timing of treatment delivery can be modified based on activity sensor 135 inputs when the arrhythmia is detected. If the subject becomes motionless coinciding with the arrhythmia detection, there is an increased confidence that the arrhythmia diagnosis is accurate and the delivery of treatment can occur sooner. If motion continues after the arrhythmia detection, the confidence of a valid detection can be decreased because lethal arrhythmias generally result in a lack of consciousness and lack of motion. In this case, the delivery of treatment can be delayed to allow time for audio voice messages to prompt the subject to respond by pressing the response button. The response button provides a responsiveness test input to the algorithm. In some embodiments, it may be desirable to never deliver a shock to a conscious subject. This method can reduce the possibility of false treatment based on invalid rhythm diagnosis due to corrupt ECG inputs caused by excessive subject movement or other environmental factors.

FIG. 5 illustrates arrhythmia detection with increased confidence by serially feeding through a subsequent confidence algorithm using input from activity sensor 135, such as a motion detector or accelerometer. Other motion detecting devices or confidence algorithms can use various motion detection criteria as desired by physicians and based upon the treatable condition or subject. The motion data can also be stored, tracked and evaluated, for example to evaluate a subject's historical motion or activity levels to detect conditions such as congestive heart failure. Such diseases can be found in subjects wearing treatment device 100. In one embodiment, treatment device 100 includes sensors 110 to monitor the subject's cardiac information. For example sensors 110 can include cardiac sensing electrodes that are positioned external to the subject to detect the subject's cardiac information. Controller 105 processes the sensed cardiac information to detect life-threatening arrhythmias, and can instruct treatment electrodes 115 to deliver treatment, such as a cardioverting or defibrillating shock. Treatment device 100 can also include a user interface to receive quality of life information. For example, the subject can enter information about the subject's lifestyle, eating and exercise habits, and how the subject currently feels. Additional sensors 110, 135 can detect subject activity or other wellness information, such as respiration or pulse rates, or temperature. In one embodiment, this subject activity and wellness information is discrete information that can be measured or sensed by sensors 110, 135, as opposed to quality of life information that may be of a more general nature such as what the subject ate or how the subject feels, or more subjective information provided by the subject or the subject's physician. In one embodiment, treatment device 100 includes at least one treatment electrode 115 configured for external positioning proximate to the subject. Controller 105 communicates with sensors 110, 135 including sensors configured to sense cardiac information (e.g., cardiac sensing electrodes) and sensors configured to detect subject activity and wellness information, (e.g., accelerometers). Controller 105 can also communicate with the user interface of monitor 130. Controller 105 receives detected cardiac information, (ECG signals), detected subject activity and wellness information, and inputted quality of life information to determine if treatment is to be applied to the subject. Controller 105 can also adjust a treatment regimen, for example by advancing or delaying its application by treatment electrodes 115. For example, controller 105 can decide to apply treatment (e.g., an electric shock from therapy electrodes 115) based on sensor 110's detected cardiac information) and can adjust the treatment regimen based on sensor 110's detected subject activity and wellness information or based on the quality of life information provided by or on behalf of the subject via a user interface. In one embodiment, controller 105 adjusts therapy based on the subject's level of activity over a period of time, where information from sensors 135 is used to determine the subject's level of activity.

In one embodiment, controller 105 controls the nature and application of a treatment regimen based on information from any of sensors 110, 135 (including, for example, cardiac sensing electrodes, other sensing electrodes, accelerometers), treatment electrodes 115, the user interface of monitor 130, and other inputs of the subject's cardiac information, subject activity and wellness information, and quality of life information. Based on this information, controller 105 can determine a treatment regimen (e.g., what type of treatment) and determine that the treatment has, is, or will be applied. Based on this information, controller 105 can also adjust the treatment regimen or the application of the treatment. Controller 105 can also control an alarm module to alert the subject or others of past, present, or pending treatment.

In one embodiment, medical condition sensors 110 and controller 105 can detect and identify heart failure indicators such as heart or respiratory rates. The subject or a service provider can view a chart or graph based on the sensed information that tracks heart failure indicators over time. The display can be on a monitor that is remote from treatment device 100 via wired or wireless communication over a network, or local to treatment device 100 as part of monitor 130. Controller 105 can generate reports that summarize trends or indicators for one or more subjects. Heart failure indicators above or below a certain threshold value can trigger an alert notification to the subject via the alarm module or to a remote doctor. The heart failure information sensed by medical condition sensors 110 can be provided to the subject or a doctor in the form of a report, either on demand or periodically as part of a routine notification schedule. The report can be sent by text message, page, automated phone call or email, and can flag trends in the subject's condition, noting changes, trends, and exceptions as they occur.

Subjects wearing treatment device 100 may suffer from heart failure and develop pulmonary edema, which involves the buildup of extravascular fluid in the lungs, (e.g., congestion). Fluid can pool in blood vessels in the lungs and become a barrier to normal oxygen exchange. In one embodiment, medical condition sensors 110 monitor impedance of the subject's thoracic cavity and controller 105 processes this sensed impedance information to detect the presence or absence of pulmonary edema, which may be an indicator of heart failure. A reduction in sensed thoracic impedance indicates an increase in thoracic fluid, and fluid depletion in the thorax indicates an increase in thoracic impedance.

In one embodiment, controller 105 and sensors 110 or treatment electrodes 115 sense and measure transthoracic impedance. This data can be collected because the subject can wear treatment device 100 substantially continuously for extended periods of time. Controller 105 can average transthoracic impedance measurements over time to identify extravascular fluid buildup. By comparing the averaged measured values with thresholds, treatment device 100 can alert the subject or a doctor of changes in the subject's condition so that treatment or medical advice can be provided.

In one embodiment, treatment device 100 measures and records respiration data by monitoring transthoracic impedance changes. For example, impedance increases as air fills the lungs, and decreases when air is exhausted from the lungs during exhaling. By monitoring these and other changes with medical sensors 110 (e.g., cardiac sensing electrodes, pulse oximeters) and activity sensors 135 (e.g., accelerometers, strain gauges, pedometers, nasal clips, expandable belts, monitoring of elastic movement of treatment device 100) controller 105 can determine the subject's respiration rate, stride, pulse, and other information. Information sensed by sensors 110, 135 can be transmitted over a network (e.g., the Internet) to a doctor on demand or as part of a periodic report. The doctor can evaluate this information to make a diagnosis.

Treatment device 100 can sense and monitor a variety of conditions and trends, such as atrial fibrillation, nocturnal heart rate, respiration rate, pulmonary sounds, heart sounds, activity trends, body position trends, heart rate variability, heart rate turbulence, and bradycardia events. For example, controller 105 can processes information detected from sensors 110, 135 (e.g., ECG signals, accelerometer information, or sound information) to detect any of these conditions. In one embodiment, medical condition sensors 110 include an ECG sensing electrode system that, together with activity sensors 135 and controller 105, detect and record metrics associated with the minimum heart rate value that typically occurs during sleep, as well as diurnal heart rate. In one embodiment, sensors 110 include an auscultation sensor that records chest and lung sound recordings to identify fluid content in the lungs. In addition, sensors 110 can detect wheezing and coughing that can indicate fluid buildup and a worsening condition. In one embodiment, activity sensors 135 can detect movement that occurs during coughing to verify an indication of a cough detected by an audio sensor. Controller 105 may also analyze sensed heart audio signals to identify changes in cardiac performance.

In one embodiment, treatment device 100 detects activity or body position trends, and analyzes this information to determine the subject's condition. Controller 100 may make this analysis, or may communicate the sensed information to a computer server, where the information is analyzed remotely. For example, the physical activity of a subject with heart failure may decrease as the heart failure condition worsens. General subject activity and movement can indicate whether the heart failure conditions are getting better or worsening, and can indicate whether treatment is working. For example, information from activity sensors 135 may be used to generate activity trends of the subject's activity level (e.g., increasing with time, decreasing with time, remaining substantially constant). This information can be generated over long periods of time when the subject is wearing treatment device 100. In one embodiment, activity sensors 135 sense subject activity, including body movement and positioning throughout the day and during sleep. Sleep positioning information may include the angle of the subject body during sleep, as sleeping in an inclined position (e.g., on a reclining chair) can indicate worsening heart failure. For example, an increasing sleep angle with time combined with decreasing activity can indicate worsening hear failure.

Treatment device 100 may detect heart rate variability, heart rate turbulence, or bradycardia. For example, medical condition sensors 110 may measure sympathetic and parasympathetic nervous system activity, and controller 105 may identify heart rate variability based on R-R intervals in ECG signals or a spectral analysis of heart rate variable frequencies. Information about these systems may be aggregated over time to identify trends.

In one embodiment, treatment device 100 is configured for self assessment entries by the subject. For example, a user interface that forms part of monitor 130 can receive quality of life information such as symptom information, body weight, and blood pressure by prompting the subject for these entries. Other self assessment entries that include quality of life information can be provided at selectable intervals, such as daily. Examples of these questions that prompt self assessment entries include: How do you feel today? How is your breathing today? Are you tired today? What is our weight today? What is your blood pressure today? What did you eat today? The subject may select from a standard list of responses, for example by indicating "worse" "the same" or "better." The subject may enter a number on a scale, for example from one to ten, or may enter measured values, for example of the subject's weight or blood pressure. In one embodiment, at least some of this information is sensed by sensors 110 or other devices, such as scales or blood pressure monitors. The subject can enter this information over the Internet, monitor 130, or a display on a battery charger unit given to patient, for example. Interfaces used for the entry of this information may be part of or remote from treatment device 100.

In one embodiment, wearable treatment device 100 includes biometric monitoring of the subject wearing treatment device 100 during initial risk assessments and during the course of treatment of a condition such as heart failure. Treatment device 100 monitors heart failure indicators and the onset of symptoms, and presents this information in a selectable and customizable form to a doctor in a periodic manner, at the doctor's choosing, or as an alert when a time sensitive condition may require quick treatment. Treatment device 100 can present this information in the form of aggregated reports that include trends with time of the subject's condition. In one embodiment, this information is aggregated in an omnibus quality of life score based on a plurality of sensed conditions. This aggregate score can be compared with a threshold value to indicate whether or when the subject requires treatment.

In one embodiment, to gather data under controlled conditions the subject undertakes physical activity, such as a six minute walk test that measures how far the subject can walk in six minutes. In this example, the subject wears treatment device 100 during the six minute walk test. Via monitor 130, treatment device 100 can guide or prompt the subject throughout the test, while protecting the subject from, for example, cardiac arrest by providing an external defibrillator. Medical condition sensors 110 (e.g., pulse oximeters) and activity sensors 135 such as pedometers can measure the subject's distance traveled, stride distance, respiration, heart rate, ECG, blood oxygen saturation, and recovery time before, during, and after the six minute walk test. The doctor can use this information to evaluate a treatment regimen or track the subject's progress. For example, the six minute walk test can be administered before and after changes to the subject's treatment regimen to evaluate the subject's progress and the efficacy of treatment. In one embodiment, the six minute walk test is modified to determine energy spent by the subject during the six minute walk, for example based on x, y, and z direction accelerometer measurements taken during the test. The subject can wear treatment device 100, and treatment device 100 can apply treatment to the subject, during the test. In one embodiment, treatment device 100 tracks the subject's exercise regimen. For example, when the exercise is walking, cycling, or aerobic activity, treatment device 100 tracks duration, distance covered, heart rate, date, respiration rate, transthoracic impedance, walking angle, heart rate variability, time spent exercising, the subject's ECG, and post-exercise recovery time. Treatment device 100 can capture this information continuously during exercise and can present this information to a doctor for analysis and record keeping. In one embodiment, treatment device 100 alerts the subject that it is time to exercise at a determined date or time. Treatment device 100 may also identify a target heart rate (or range) and prompt the subject in real time to exercise with greater or lesser intensity in order to maintain a heart rate substantially at the target heart rate and to properly warm up and cool down before and after exercising. The target range can be adjusted based on information provided by sensors 110, 135.

Throughout the exercise regimen, treatment device 100 can monitor, record, and report information related to the subject's activity together with date and time information. Reports or summaries of this subject activity can be provided to a doctor, and can flag for the doctor's attention any conditions or changes that may have occurred during exercise. Treatment device 100 may also act as a diet monitor that sets up and tracks the subject's eating habits. This information can be reported to a doctor. In one embodiment, treatment device 100 monitors a treatment regimen that includes special dietary guidelines, such as a low fat, low calorie, or low salt diet. The subject can enter information about the food the subject is eating in real time, via a user interface of monitor 130. In one embodiment, the user interface includes a bar code scanner to scan packaged food bar codes and retrieve their nutritional information from a database. In some embodiments, treatment device 100 monitors the subject's diet and weight in parallel and adjusts a recommended diet regimen of the subject to adjust or maintain the subject's weight. For example, treatment device 100 can normalize food intake to overall subject energy, deduced by controller 105 from accelerometer readings, over a period of time to identify a diet regimen.

Further examples of the information sensed and evaluated by the components of wearable treatment device 100 include the following:

Subject Movement During Arrhythmia

Activity sensors 135, such as an accelerometer can be used to determine a subject's body state during the detection of an arrhythmia. They can also be used to detect if a mechanically noisy environment is the cause of erroneous arrhythmia detection.

Subject Movement Used in the Confidence Algorithm Factor

In one embodiment, a confidence algorithm, which can be influenced by many inputs including the subject's body state as determined by activity sensors 135, is used to determine if a subject's heart arrhythmias requires defibrillation by treatment device 100.

In one embodiment, cardiac treatment is not required if the subject is conscious and occurs only when the subject is unconscious. By using activity sensors 135 the subject body state can be monitored. In one embodiment, when there has been no change in subject body state for a period of time as detected by activity sensors 135 then there will be an increased confidence of the algorithm that the subject is unconscious. For example, if a change in subject body state is detected by activity sensors 135, such as an accelerometer, then there will be a decreased confidence of the algorithm that the subject is unconscious. Treatment device 100 can adjust the treatment regimen to, for example, hasten the application of treatment if a high level of confidence exists that the subject is unconscious. If subject motion is detected while other sensors 110 and algorithms processed by controller 105 indicate that a treatable rhythm is present, treatment delivery can be delayed to provide the subject additional time to respond to system messaging.

False Arrhythmia Detection Due to Physical Motion

Controller 105 can detect a false arrhythmia due to physical motion. For example, sensors 110 or wire 125 can move against the body or clothing, creating false deviations in the subject's ECG. If an arrhythmia is detected and vibration or high subject/equipment acceleration is detected, then the subject can be alerted to this condition. Monitor 130 or an alarm module can notify the subject. This information may also be applied to the treatment confidence algorithm thereby causing a decrease in confidence given that the physical motion can cause a false positive detection. Use of activity sensors 135 can reduce undesired treatment of false arrhythmias.

Correlation of ECG Artifact with Belt Motion

Motion of the belt or other treatment device 100 component may cause interference with ECG signal pickup and possible false detections. The signals obtained from activity sensors 135 or other sensors 110 can be correlated with an ECG signal to determine if ECG signal contamination exists. The quality of the correlation can be used by controller 105 as an additional confidence factor in the arrhythmia detection algorithm. If an arrhythmia is detected and there is a high degree of correlation between the ECG signal and a signal from activity sensor 135, the confidence in the arrhythmia detection can be reduced. No signal correlation indicates increased confidence that the arrhythmia detection is accurate.

Treatment Verification

Activity sensors 135, such as accelerometers may also be used to verify that a treatment has been applied by detecting sudden movements or muscle spasms in the subject immediately following the treatment. Often after defibrillation the subject's muscles spasm from the energy pulse. The muscle spasm can cause detectable movements on activity sensors 135 similar to convulsing.

Detection of Bystanders/Unsuccessful Defibrillation

Post shock motion of the subject after several unsuccessful defibrillation attempts may indicate the presence of bystanders. The bystanders could be rescue personnel such as an EMT. In this case monitor 130 or an associated alarm module can generate audio or visual alarms or voice messages to inform the bystander of the equipment and treatment status. Controller 105 can adjust the timing of additional shocks (for example by delaying or canceling them) to prevent a shock to the bystanders or rescue personnel.

Post Shock Motion Detection

When a shock is delivered, the subject may move suddenly and then return to a state where there is a lack of motion. If no further motion is detected, controller 105 can determine with a high confidence level that the arrhythmia is still present. This information can be used by controller 105 as an additional post-shock confidence factor for the detection algorithm and that a continuing cardiac condition exists. If post-shock motion continues or if the subject body position changes from a horizontal to vertical position, controller 105 can determine that there is high confidence that the defibrillation was successful and additional shocks or other treatment can be delayed. Based on post shock motion, treatment device 100 can also detect and control pacing of the subject.

Belt Quality Feedback

Treatment device 100 may include a belt for proper positioning on the subject and to house treatment device 100 components. Overall belt quality can be examined by gathering data using activity sensors 135 during certain failure states such as sensor 110 fall-off and treatment electrode 115 fall-off detection.

Reduce Electrode and Therapy Pad Fall-Offs

If one of sensors 110 or treatment electrodes 115 fall off of the subject, controller 105 can record the subject's body state during the fall-off event based on information from sensors 110, 135 or information input by the subject via a user interface. Subject positions include sitting up, lying down; left side, right side. If controller 105 identifies vibration or the subject falling then that information can be recorded and evaluated by controller 105 since it might be the cause of the falloff event. Over time, controller 105 can use this information to determine positions that may tend to cause fall-offs of treatment device 100 components. This information can then be used to improve the belt design reducing and possibly eliminating the fall-offs in those certain activities or positions. This information can also be used to train the subject and those assisting the subject as to how to wear and use treatment device 100 and its components, as well as to establish instructions for future use of treatment device 100. An example would be if post analysis of data over a several month period of time shows that 75% of ECG fall-offs occur when the subject is laying on their left side then the belt design on the left side could be examined to determine what might be making it susceptible to fall-offs in that subject position.

Provide Recommendations to Subjects

Activity sensor 135 data collected over time could also be used to inform subjects of body states that tend to be more comfortable. Subjects who have worn the device for an extended time will most likely have experimented with different positions (sleeping positions, sitting positions, etc.) and will tend to use the most comfortable ones. This data can be provided to controller 105, stored, and used to improve the belt for the other positions and also provide recommendations to new subjects.

Improve Belt Comfort Data collected by sensors 110 during subject use can be used to improve the comfort of the treatment device 100 when worn by studying subject sleep habits, or habits during other selected activities. For example, if 80% of the subjects tend to sleep on their right side then the assumption can be made that something about the belt makes it less comfortable for the subjects to lie on their left side. With this information controller 105 can determine what about that position causes the belt to be uncomfortable and engineering can be performed to improve treatment device 100 comfort.

Belt Self Diagnostics

Self diagnostics may also be provided such as a Belt Node Tactile Stimulator (vibration/acceleration) self test. For example, treatment device 100 may include a tactile stimulator or other subject notification device. The tactile stimulator may include a motor with an unbalancing weight on its shaft. When the motor is on, it causes the belt to vibrate much like a cell-phone in vibration mode. When the tactile stimulator is activated, an activity sensor 135, such as an accelerometer in node 120 can detect vibrations from the tactile stimulator to verify that node 120 is vibrating and that the tactile stimulator is working. The tactile stimulator can be housed in node 120, with monitor 130, or the alarm module.

Subject Notification of Physical Events

Controller 105 can use activity sensor 135 information to provide feedback to the subject regarding mechanical events, or to adjust audio volume outputs of the alarm module or monitor 130 based on the current state of the subject.

Equipment Abuse Notification

If certain mechanical conditions that may lead to equipment damage such as mechanical shock or vibration are detected by activity sensors 135 then the controller 105 can instruct monitor 130 or the alarm module to notify the subject of such conditions and advise the subject of the condition.

If monitor 130 or belt is dropped, or if they are hit with some other object causing a force greater than a predefined acceptable force, then monitor 130 or the alarm module can provide an audio, visual, or haptic indication to the subject that the event has occurred and warn against allowing such an event to occur again.

If continuous vibration above a certain predefined acceptable threshold is detected for a period of time, then monitor 130 or the alarm module may also provide a warning to the subject. Such vibration could lead to sensor 110 or treatment electrode 115 fall-off, or even cause false arrhythmia detection if enough physical motion is applied to the sensors 110, treatment electrodes 115, wires 125, or other components.

Adjust Device Alarm Volumes

If information from activity sensors 135 indicates that the subject's body state is unchanged for a period of time, and the subject is either lying or sitting down then controller 105 can determine that the subject is sleeping and can increase the audio volume output of any audio message if necessary to awaken the subject. Controller 105 may also enable the tactile stimulator to awaken the subject in the event of a critical audio message.

Adjust Display Rotation

Information from activity sensors 135 can be used by controller 105 to determine the proper position of monitor 130 to deliver a visual message to the subject or for initial subject setup by care givers. For visual messages to the subject, since monitor 130 can be positioned approximately at the subject's mid section, the display of information by monitor 130 may appear upside down (rotated 180 degrees) with respect to monitor 130. However, during setup, when the subject is fitted with treatment device 100 and when its components are positioned, monitor 130 could be held right side up in front of the skilled personnel. As a result, the display would be right side up.

Detect Equipment Abuse

Controller 105 can detect abuse of treatment device 100 and its components during use as well as during shipping. This abuse can be determined by parameters such as number of times dropped and intensity. Detection of abuse can trigger such actions as internal diagnostics, auto download, and equipment service recommendations.

Equipment Drop Detection

If activity sensors 135 detect a mechanical shock, for example to monitor 130 above a pre-determined acceptable threshold, then controller 105 can identify and record a drop event. Other parameters such as date/time stamp and current operating mode can be identified and recorded as well. The date/time stamp can allow correlation between monitor 130 location and the damaging event allowing further information to be obtained using the carrier tracking numbers if such damage occurred during shipping.

If it is not during shipping and is during use of treatment device 100 by the subject, and there is some form of treatment device 100 malfunction after the drop then that could be tied to the root cause of the equipment failure. Such information could be used to advise subjects of the types of mechanical shocks that may damage the equipment or components of treatment device 100. It also may be used to improve the robustness of the equipment to survive such forces in the future.

Equipment Service Recommendation

If activity sensors 135 records a mechanical shock above a predefined acceptable threshold, or if a predefined acceptable number of mechanical shocks have occurred, monitor 130 can display a message indicating that the equipment should be serviced. Controller 105 can also, during the next download, notify the manufacturer that treatment device 100 should be serviced.

Internal Diagnostics

Logic devices that are part of activity sensor 135, monitor 130, or node 120 may constitute at least part of controller 105. If activity sensor 135 does detect an excessive mechanical shock on the belt or monitor 130 then controller 105 may initiate internal self-diagnostics. Activity sensor 135, monitor 130, and node 120 may include circuitry to allow most of its components to be tested with self diagnostics.

Auto Download to Manufacturer

If there is a significant mechanical shock to treatment device 100 components or equipment such as the belt or monitor 130, then controller 105 may communicate with the manufacturer via a communications network to request service.

Monitor Subject Activity Over Time

Data provided by activity sensor 135 or medical condition sensors 110 can be measured and stored over time to study subject activity. Subject activity data can be used to provide feedback to doctors about a subject's specific condition.

Subject Activity Data and Treatment

After applying treatment, subject activity data taken before, up to, and including the event can be downloaded from treatment device 100 to a remote data storage unit. This information can also be recorded locally at treatment device 100. This data can be collected among a plurality of subjects and used to make correlations between subject activity derived from sensors 110 and the probability of a cardiac event or other condition that requires treatment occurring. These correlations can be used to take precautionary measures with subjects who have similar activities as those who had past treatment events.

Subject Activity Data and Doctor Feedback

Subject activity data can be used over a period of time by doctors or data evaluation systems to determine if proper subject activity levels are met. For example, a doctor can analyze the data to determine that there is low subject activity, or that the subject is performing recommended exercises. The doctor can also monitor the subject's real time activity level and corresponding heart rate data. Subjects who are experiencing congestive heart failure can be monitored for physical activity and at rest body position. Gradual reduction in subject activity indicated by lack of motion can indicate a worsening of the congestive heart failure condition. Body position at rest can also indicate subject deterioration if body position at rest is primarily vertical since congestive heart failure subjects may have difficulty resting in a horizontal position.

Figure 6:
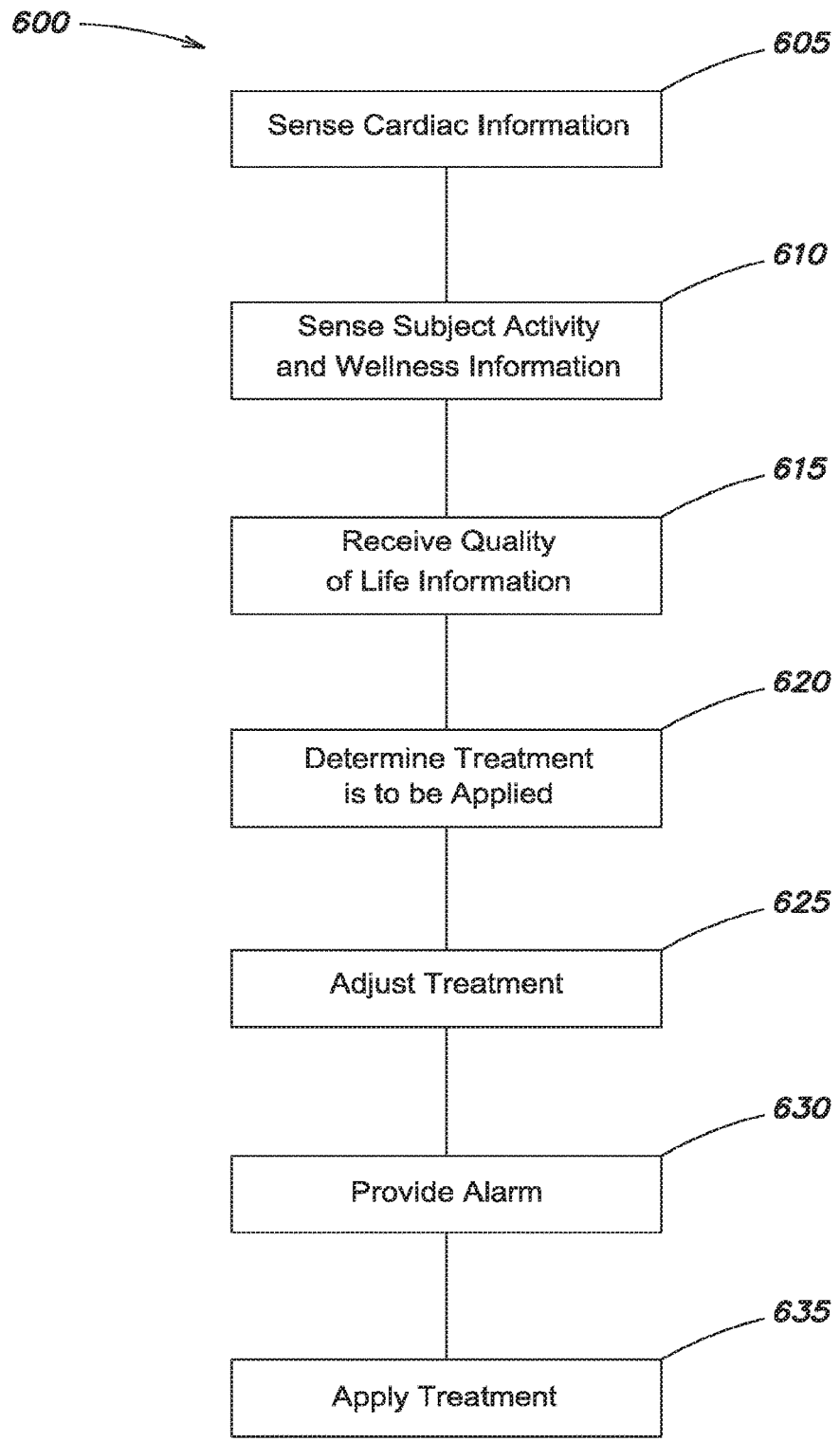
FIG. 6 depicts a flow chart for a method of monitoring and treating a subject in accordance with an embodiment.

FIG. 6 depicts a flow chart for a method 600 of monitoring and treating a subject. In one embodiment, method 600 includes an act of sensing cardiac information of a subject (ACT 605). For example, sensing cardiac information (ACT 605) may include detecting ECG (electrocardiogram) signals or other information related to electrical or mechanical activity of the subject's heart. In one embodiment, dry external electrodes are configured external to the subject to sense (ACT 605) cardiac information. Internal electrodes may be used as well. Sensors used to sense (ACT 605) cardiac information can be part of a wearable subject treatment device that includes an external defibrillator. In one embodiment, sensing cardiac information (ACT 605) includes sensing information indicative of heart failure or other medical conditions.

In one embodiment, method 600 includes the act of sensing at least one of subject activity and wellness information (ACT 610). For example, internal or external sensors proximate to the subject's body can sense (ACT 610) pulse, breathing, temperature, blood pressure, or fatigue information, for example. In one embodiment, sensing activity and wellness information (ACT 610) includes detecting subject movement, lack thereof, position, or orientation. Sensing activity or wellness information (ACT 610) may include detecting tangible medical or physical condition or information indicative of a subject's overall health, as well as changes in health-related measurements or conditions with time.

Method 600 may also include at least one act of receiving quality of life information (ACT 615). The quality of life information may be received from the subject, or on the subject's behalf from a physician or someone acting on the subject's behalf. In one embodiment, quality of life information is received (ACT 615) by a user interface of a wearable treatment device. For example, the quality of life information may be received (ACT 615) via direct manual entry into the user interface, or remotely via one or more wired or wireless networks. Receiving quality of life information (ACT 615) may include receiving information about the subject's lifestyle, such as dietary, activity, or exercise habits, when the subject last took a particular action, or information about how the subject feels.

In one embodiment, method 600 includes acts of determining whether or not treatment is to be applied (ACT 620) and adjusting the determined treatment (ACT 625). For example, treatment (e.g., an electric shock) can be determined to be applied (ACT 620) based on the detected (ACT 605) cardiac information. In this example, sensed (ACT 605) cardiac information may indicate that the subject is experiencing a cardiac event and in need of pacing or defibrillation. Adjusting the treatment (ACT 625) may include time shifting the application of the treatment, or delaying application of the treatment pending confirmation of the subject's condition, based on the subject's sensed (ACT 610) activity and wellness information. For example, method 600 can determine (ACT 620) that treatment is not to be applied due to a high heart beat, when sensed (ACT 610) subject activity and wellness information indicates that the subject is intensely exercising, and that this may be the cause of the elevated heart beat. In this example, application of pacing or other treatment can be delayed (ACT 620) until it is determined that the subject is no longer exercising yet still has an elevated heart rate.

In one embodiment, method 600 includes an act of providing an alarm (ACT 630). For example, an alarm can be provided (ACT 630) by alerting the subject or other person of treatment. The alarm may be audio, visual, haptic, or combinations thereof, and can alert the subject and others in the vicinity of the subject of a treatment regimen. In one embodiment, providing the alarm (ACT 630) includes alerting a doctor or health care provider that treatment has, is, or will be applied to a subject where the doctor is located remotely from the subject. For example, the alarm may be provided (ACT 630) when the subject is on the street, or at home. In this example, the alarm can be provided remotely via wired or wireless communications through a communications network to the doctor who may be present in a hospital or office.

In some embodiments, providing the alarm (ACT 630) includes alerting the subject or other person of a treatment regimen subsequent to sensing the subject's cardiac information (ACT 605). Providing the alarm (ACT 630) may also include alerting the subject or other person of a treatment regimen prior to an act of applying treatment to the subject (ACT 635). In one embodiment, applying treatment to the subject (ACT 635) includes applying an electrical shock or current to the subject as part of a defibrillation or pacing treatment regimen. In some embodiments, applying treatment (ACT 635) occurs subsequent to the act of alerting the subject or another person that treatment has been applied, is being applied, or will be applied.

Figure 7:
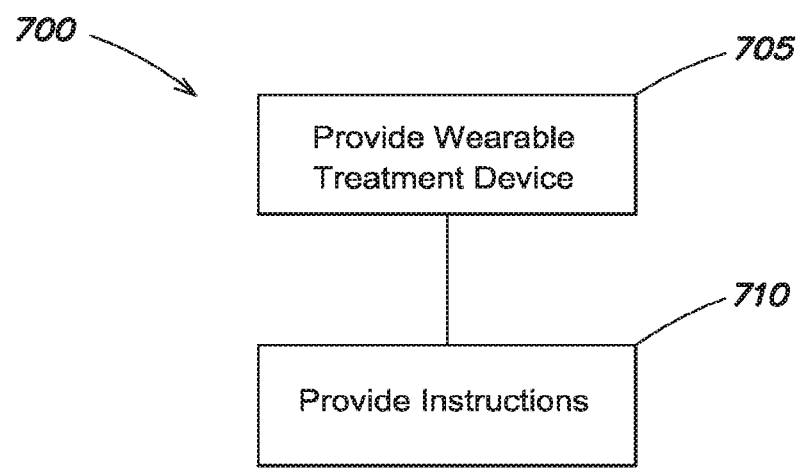
FIG. 7 depicts a flow chart for a method of monitoring and treating a subject in accordance with an embodiment.

FIG. 7 depicts a flow chart for a method 700 of monitoring and treating a subject. In one embodiment, method 700 includes an act of providing the wearable treatment device (ACT 705). For example, providing the device (ACT 705) may include providing a garment in the general form of a vest or shirt that may include at least one strap, belt, pocket or receptacle. In one embodiment, providing the wearable treatment device (ACT 705) includes providing a device that includes a cardiac sensing electrode to detect cardiac information (e.g., ECG) of the subject, and a treatment electrode to apply electric current to the subject as part of, for example, a defibrillation or pacing treatment. Providing the device (ACT 705) may also include providing a user interface to receive quality of life information from the subject. This may include factual data about the subject's lifestyle, as well as the subject's opinion as to how the subject feels or the subject's health. Providing the device (ACT 705) may also include providing a garment with an activity sensor, such as one or more motion sensors or accelerometers to detect subject activity and wellness information indicative of a general wellness of the subject.

In one embodiment, providing the device (ACT 705) includes providing a controller. The controller communicates with the cardiac sensing electrode, the treatment electrode, the user interface, and the sensor to receive the detected cardiac information, the quality of life information, and the detected subject activity and wellness information. The controller can also determine that treatment is to be applied to the body of the subject based upon the detected cardiac information, and can adjust the treatment based on at least one of the detected subject activity and wellness information and the quality of life information. In one embodiment, providing the device (ACT 705) includes providing an alarm module. The alarm module can provide an alarm to indicate treatment has, is, or will be applied to the body of the subject.

In one embodiment, method 700 includes an act of providing instructions (ACT 710). This may include providing instructions to operate the wearable treatment device. For example, providing instructions (ACT 710) can include providing at least one instruction to position at least one of the cardiac sensing electrode, the therapy electrode, and the activity sensor on the subject, and any other device components on the subject. Providing instructions (ACT 710) may also include providing instructions to wear or position the wearable treatment device or any of its components on the subject.

Having now described some illustrative embodiments of the invention, it should be apparent to those skilled in the art that the foregoing is illustrative and not limiting, having been presented by way of example. In particular, although many of the examples presented herein involve specific combinations of method acts or system elements, it is understood that those acts and those elements may be combined in other ways to accomplish the same objectives. Acts, elements and features discussed only in connection with one embodiment are not intended to be excluded from a similar role in other embodiments.

Note that in FIGS. 1 through 7, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes data signals embodied in one or more of a computer disk (magnetic, or optical (e.g., CD or DVD, or both)), non-volatile memory, tape, a system memory, and a computer hard drive.

From the foregoing, it will be appreciated that the wearable treatment device described herein is worn by the subject and senses information about the subject's activity, wellness, and quality of life via direct sensing or user provided data entries. The treatment device can determine if treatment is needed based on the subject's physical condition, can adjust treatment regiments based on sensed information, and can apply treatment to the subject as necessary. The wearable treatment device can gather information about the subject's health in real time over a substantially continuous period. This information can be aggregated to form a comprehensive medical history of the subject, which can be used to determine if past treatment regimens are successful and if modifications should be made.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

Publications, patents, and patent documents referred to in this document are incorporated by reference herein in their entirety, as though individually incorporated by reference. In the event of inconsistent usages between this document and those documents so incorporated by reference, the usage in the incorporated references is supplementary to that of this document; for irreconcilable inconsistencies, the usage in this document controls.

References to "or" may be construed as inclusive, so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

One skilled in the art will realize the systems and methods described herein may be embodied in other specific forms without departing from the characteristics thereof. For example, the wearable treatment device can be used outside a hospital setting to protect the subject, apply treatment, and create medical history simultaneously. The wearable treatment device may also include a series of electrodes and other elements that are disposed about the subject and do not constitute an actual garment. The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A wearable treatment device for treatment of a subject, comprising:
   a plurality of cardiac sensing electrodes configured to be positioned outside a body of the subject and to detect cardiac information of the subject;
   at least one treatment electrode configured to be positioned outside the body of the subject and to apply a treatment to the subject;
   an activity sensor configured to detect activity information of the subject including at least one of body position of the subject and body movement of the subject;
   a sensor configured to be positioned outside the body of the subject and to sense a transthoracic impedance of the subject; and
   a controller disposed in the wearable treatment device and configured to substantially continuously monitor the detected cardiac information of the subject, the controller communicatively coupled to the plurality of cardiac sensing electrodes, the at least one treatment electrode, and the sensor, the controller configured to
   receive and record the detected cardiac information, the activity information, and the sensed transthoracic impedance of the subject,
   determine whether the treatment should be applied to the body of the subject based upon the detected cardiac information,
   initiate the treatment of the subject in response to a determination that the treatment should be applied to the body of the subject,
   monitor the activity information of the subject to detect trends over time that are indicative of changes in a heart failure condition of the subject, and
   monitor the sensed transthoracic impedance of the subject to detect changes in extravascular fluid in lungs of the subject over time that are indicative of changes in the heart failure condition of the subject.

2. The wearable treatment device of claim 1, further comprising a user interface communicatively coupled to the controller and configured to receive quality of life information from the subject.

3. The wearable treatment device of claim 2, wherein the quality of life information identifies at least one of a fatigue level and a breathing level of the subject.

4. The wearable treatment device of claim 2, wherein the quality of life information identifies information about at least one of the subject's lifestyle, body weight, blood pressure, eating and exercise habits, symptom information, fatigue information, breathing level, and how the subject currently feels.

5. The wearable treatment device of claim 2, further comprising at least one additional sensor positioned outside the body of the subject and communicatively coupled to the controller, the at least one additional sensor being configured to detect wellness information indicative of a general wellness of the subject.

6. The wearable treatment device of claim 5, wherein the controller is further configured to adjust the treatment based on the detected cardiac information and at least one of the detected activity information, the detected wellness information, and the quality of life information.

7. The wearable treatment device of claim 5, wherein the controller can provide at least one of the detected cardiac information, the detected activity information, and the detected wellness information to a computer server via a network.

8. The wearable treatment device of claim 2, wherein the quality of life information is received from the subject in response to questions posed to the subject via the user interface.

9. The wearable treatment device of claim 8, wherein the questions are posed to the subject at selectable intervals.

10. The wearable treatment device of claim 2, wherein the user interface is configured to prompt the subject to provide the quality of life information.

11. The wearable treatment device of claim 1, further comprising at least one additional sensor positioned outside the body of the subject and communicatively coupled to the controller, the at least one additional sensor being configured to detect wellness information indicative of a general wellness of the subject.

12. The wearable treatment device of claim 11, wherein the controller can provide at least one of the detected cardiac information, the detected activity information, and the detected wellness information to a computer server via a network.

13. The wearable treatment device of claim 11, wherein the at least one additional sensor is configured to detect at least one of blood pressure, blood oxygen level, respiration, hypovolemia, and temperature.

14. The wearable treatment device of claim 1, further comprising an auscultation sensor positioned outside the body of the subject and communicatively coupled to the controller, the auscultation sensor being configured to detect one or more subject conditions based on chest and lung sound recordings.

15. The wearable treatment device of claim 1, wherein the controller is further configured to monitor the activity information throughout the day and during sleep.

16. The wearable treatment device of claim 1, wherein the controller is further configured to detect, from the activity information, that the subject's body position is in one of an upright position, a prone position, and a sleeping position.

17. The wearable treatment device of claim 1, wherein the activity information of the subject includes body position of the subject and body movement of the subject.

18. The wearable treatment device of claim 1, wherein the sensor configured to be positioned outside the body of the subject and to sense the transthoracic impedance of the subject is distinct from the plurality of cardiac sensing electrodes and the at least one treatment electrode.

19. A wearable monitoring device for monitoring a subject, comprising:

a plurality of cardiac sensing electrodes configured to be positioned outside a body of the subject and to detect cardiac information of the subject;

an activity sensor configured to detect activity information of the subject including at least one of body position of the subject and body movement of the subject;

a sensor configured to be positioned outside the body of the subject and to sense a transthoracic impedance of the subject;

a user interface configured to receive quality of life information from the subject; and a controller disposed in the wearable monitoring device and configured to substantially continuously monitor the detected cardiac information of the subject, the controller communicatively coupled to the plurality of cardiac sensing electrodes and the sensor, the controller configured to receive and record the detected cardiac information, the activity information, and the sensed transthoracic impedance of the subject, determine one or more arrhythmias based on the detected cardiac information, monitor the activity information of the subject to detect trends over time that are indicative of changes in a heart failure condition of the subject, and monitor the sensed transthoracic impedance of the subject to detect changes in extravascular fluid in lungs of the subject over time that are indicative of changes in the heart failure condition of the subject.

20. The wearable monitoring device of claim 19, wherein the quality of life information identifies at least one of a fatigue level and a breathing level of the subject.

21. The wearable monitoring device of claim 19, wherein the quality of life information identifies information about at least one of the subject's lifestyle, body weight, blood pressure, eating and exercise habits, symptom information, fatigue information, breathing level, and how the subject currently feels.

22. The wearable monitoring device of claim 19, further comprising at least one additional sensor positioned outside the body of the subject and communicatively coupled to the controller, the at least one additional sensor being configured to detect wellness information indicative of a general wellness of the subject.

23. The wearable monitoring device of claim 22, wherein the controller can provide at least one of the detected cardiac information, the detected activity information, and the detected wellness information to a computer server via a network.

24. The wearable monitoring device of claim 22, wherein the at least one additional sensor is configured to detect at least one of blood pressure, blood oxygen level, respiration, hypovolemia, and temperature.

25. The wearable monitoring device of claim 19, wherein the quality of life information is received from the subject in response to questions posed to the subject via the user interface.

26. The wearable monitoring device of claim 25, wherein the questions are posed to the subject at selectable intervals.

27. The wearable monitoring device of claim 19, wherein the user interface is configured to prompt the subject to provide the quality of life information.

28. The wearable monitoring device of claim 19, wherein the one or more arrhythmias include atrial fibrillation.

29. The wearable monitoring device of claim 19, wherein the controller wirelessly communicates the detected cardiac information and the detected quality of life information to a central server for processing and presentation to a doctor for review and analysis.

30. The wearable monitoring device of claim 19, wherein the controller is further configured to determine an average of the sensed transthoracic impedance of the subject over time and to alert at least one of the subject and a doctor to changes in the average indicative of extravascular fluid increase.

31. A method for monitoring a subject comprising:

receiving and recording cardiac information of the subject, the cardiac information being received from a plurality of cardiac sensing electrodes positioned outside a body of the subject;

receiving and recording a sensed transthoracic impedance of the subject, the sensed transthoracic impedance being received from a sensor positioned outside the body of the subject;

determining one or more arrhythmias based on the detected cardiac information; and monitoring the sensed transthoracic impedance of the subject to detect changes in extravascular fluid in lungs of the subject over time that are indicative of changes in a heart failure condition of the subject.

32. The method of claim 31, further comprising receiving quality of life information from the subject.

33. The method of claim 32, wherein the quality of life information identifies at least one of a fatigue level and a breathing level of the subject.

34. The method of claim 31, further comprising detecting activity information of the subject including at least one of body position of the subject and body movement of the subject.

35. The method of claim 34, further comprising monitoring the activity information throughout the day and during sleep.

36. The method of claim 34, further comprising detecting, from the activity information, that the subject's body position is in one of an upright position, a prone position, and a sleeping position.

* * * * *

UNITED STATES PATENT AND TRADEMARK OFFICE
CERTIFICATE OF CORRECTION

Page 1 of 1

PATENT NO. : 10,271,791 B2
APPLICATION NO. : 15/649739
DATED : April 30, 2019
INVENTOR(S) : Edward J. Donnelly et al.

It is certified that error appears in the above-identified patent and that said Letters Patent is hereby corrected as shown below:

In the Specification

Column 8, Line 5, delete "habits)", insert --habits),--
Column 10, Line 22, delete "interface)", insert --interface),--
Column 12, Line 48, delete "switch)", insert --switch),--
Column 14, Line 5, delete "information)", insert --information),--
Column 15, Line 11, delete "oximeters)", insert --oximeters),--
Column 15, Line 14, delete "100)", insert --100),--

In the Claims

Claim 29, Column 28, Line 14, after "the" delete "detected"

Signed and Sealed this
Twenty-fifth Day of June, 2019

Andrei Iancu
*Director of the United States Patent and Trademark Office*